(12) United States Patent
Takezawa

(10) Patent No.: US 12,133,750 B2
(45) Date of Patent: Nov. 5, 2024

(54) X-RAY IMAGING APPARATUS

(71) Applicant: SHIMADZU CORPORATION, Kyoto (JP)

(72) Inventor: Hidetaka Takezawa, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 264 days.

(21) Appl. No.: 17/629,070

(22) PCT Filed: May 7, 2020

(86) PCT No.: PCT/JP2020/018557
§ 371 (c)(1),
(2) Date: Jan. 21, 2022

(87) PCT Pub. No.: WO2021/033370
PCT Pub. Date: Feb. 25, 2021

(65) Prior Publication Data
US 2022/0273251 A1 Sep. 1, 2022

(30) Foreign Application Priority Data
Aug. 20, 2019 (JP) .................. 2019-150679

(51) Int. Cl.
*A61B 6/00* (2024.01)
*A61B 6/04* (2006.01)
(52) U.S. Cl.
CPC .......... *A61B 6/0407* (2013.01); *A61B 6/4441* (2013.01); *A61B 6/481* (2013.01)
(58) Field of Classification Search
CPC .......... A61B 6/00; A61B 6/04; A61B 6/0407; A61B 6/4441; A61B 6/481; A61B 6/0487; A61B 6/504; A61B 6/5241; A61B 6/54
See application file for complete search history.

(56) References Cited

U.S. PATENT DOCUMENTS

| | | | |
|---|---|---|---|
| 8,019,041 B2 * | 9/2011 | Tomisaki | A61B 6/481 378/62 |
| 2004/0114717 A1 | 6/2004 | Kato | |
| 2018/0214103 A1 | 8/2018 | Okubo | |

FOREIGN PATENT DOCUMENTS

| | | |
|---|---|---|
| JP | 2004057506 A | 2/2004 |
| JP | 2004194697 A | 7/2004 |

(Continued)

OTHER PUBLICATIONS

Notice of Reasons for Refusal dated Dec. 13, 2022 for corresponding Japanese patent application No. JP 2021-540630.

(Continued)

*Primary Examiner* — Jurie Yun
(74) *Attorney, Agent, or Firm* — Muir Patent Law, PLLC

(57) ABSTRACT

The X-ray imaging apparatus (100) is provided with an imaging unit (2), a moving mechanism (4), and an image processing unit (17) for generating a subject image (42). The image processing unit is configured to set a reference plane (34) that is an imaging region when generating a subject image and generate the subject image on the reference plane. In a case where there is a plurality of X-ray images in which pixel corresponding points are reflected, the image processing unit is configured to select the pixels corresponding to the pixel corresponding points in the X-ray image in which the pixel corresponding points are reflected to determine pixel values of the pixel corresponding points.

13 Claims, 15 Drawing Sheets

(56) References Cited

FOREIGN PATENT DOCUMENTS

| | | |
|---|---|---|
| JP | 2005046444 A | 2/2005 |
| JP | 2005296332 A | 10/2005 |
| JP | 2018121745 A | 8/2018 |

OTHER PUBLICATIONS

Written Opinion by the International Search Authority for PCT application PCT/JP2020/018557 dated Jul. 14, 2020, submitted with a machine translation.

\* cited by examiner

Generation of an elongated image

Third Modification

Third Modification

Fourth Modification

Fourth Modification

Fifth Modification

Fifth Modification

Sixth Modification

X-RAY IMAGING APPARATUS

TECHNICAL FIELD

The present invention relates to an X-ray imaging apparatus, specifically to an X-ray imaging apparatus for generating a subject image based on images captured at a plurality of imaging positions.

BACKGROUND OF THE INVENTION

Conventionally, an X-ray imaging apparatus for generating a subject image based on images captured at a plurality of imaging positions is known. Such an X-ray imaging apparatus is disclosed, for example, in Japanese Unexamined Patent Application Publication No. 2004-57506.

Japanese Unexamined Patent Application Publication No. 2004-57506 discloses an X-ray imaging apparatus provided with a top board for placing a subject thereof, an X-ray tube for irradiating the subject with X-rays, an X-ray detector, and a vertically movable frame for holding the X-ray tube and the X-ray detector. The vertically movable frame disclosed in Japanese Unexamined Patent Application Publication No. 2004-57506 is mounted on a ceiling rail or a floor rail and is configured to be capable of moving the X-ray tube and the X-ray detector in a direction along a body axis of a subject.

The X-ray imaging apparatus disclosed in Japanese Unexamined Patent Application Publication No. 2004-57506 is configured to capture a plurality of X-ray images while moving the vertically movable frame. The X-ray imaging apparatus disclosed in Japanese Unexamined Patent Application Publication No. 2004-57506 is configured to capture a plurality of X-ray images in a state in which a plurality of X-ray images is overlapped. The X-ray imaging apparatus disclosed in Japanese Unexamined Patent Application Publication No. 2004-57506 is configured to generate a single elongated image by superimposing the overlapping portions of the plurality of X-ray images. Such an elongated image is particularly used in the case of performing a surgical operation in which the imaging range is required to be largely moved because it does not fit in a single X-ray image, such as a case in which a contrast agent is administered to confirm a stenotic site or a branch portion of a blood vessel in a lower limb.

PRIOR ART DOCUMENT

Patent Document

Patent Document 1: Japanese Unexamined Patent Application Publication No. 2004-57506

SUMMARY OF THE INVENTION

Problems to be Solved by the Invention

As shown in FIG. 1 of Japanese Unexamined Patent Application Publication No. 2004-57506, X-rays are emitted radially from an X-ray tube. Therefore, the incident angle of the X-rays may differ at the overlapped portion of X-ray images depending on the position of the X-ray tube when the X-ray images were captured. When the incident angle of the X-rays differs, a disparity occurs in the overlapping portion of each X-ray image. In such a case, if an elongated image (subject image) is generated by joining the overlapping portions, the joined portion becomes unnatural, which makes it difficult to generate a smooth subject image.

The present invention has been made to solve the aforementioned problems. It is an object of the present invention to provide an X-ray imaging apparatus capable of generating a smooth subject image even in a case where a subject image is generated based on a plurality of images captured while changing the imaging position.

Means for Solving the Problem

In order to attain the above-described object, an X-ray imaging apparatus according to one aspect of the present invention includes:

an imaging unit including an X-ray source for irradiating a subject with X-rays and an X-ray detection unit for detecting the X-rays transmitted through the subject, the imaging unit being configured to capture an image;

a moving mechanism including a top board for placing the subject thereon, the moving mechanism being capable of moving at least one of the top board and the imaging unit to change a relative position between the top board and the imaging unit;

an image processing unit configured to acquire a plurality of images while changing the relative position by the moving mechanism and generate a subject image based on the plurality of images, wherein the image processing unit is configured to set a reference plane that is an imaging region when generating the subject image based on the plurality of images and determine pixel values of a plurality of points included in the reference plane to generate the subject image on the reference plane, and wherein in a case where there is a plurality of images in which the points are reflected, the image processing unit is configured to select a pixel corresponding to the point in the image in which the point is most clearly reflected among the plurality of images to determine the pixel value of the point.

Effects of the Invention

In the X-ray imaging apparatus according to one aspect of the present invention, as described above, the image processing unit is provided with an image processing unit. The image processing unit is configured to set a reference plane that is an imaging region when generating the subject image based on the plurality of images and determine the pixel values of the plurality of pixel corresponding points included in the reference plane to generate the subject image on the reference plane. Further, in a case where there is a plurality of images in which the pixel corresponding points are reflected, the image processing unit is configured to select the pixel corresponding to the pixel corresponding point in the image in which the pixel corresponding point is most clearly reflected among the plurality of images to determine the pixel value of the pixel corresponding point. With this, the pixel value of each pixel corresponding point on the reference plane is selected from the pixel corresponding to the pixel corresponding point in the image in which the pixel corresponding point is most clearly reflected among the plurality of images. Therefore, it is possible to generate a subject image based on the pixel value selected from one pixel corresponding to each pixel corresponding point on the reference plane. For this reason, unlike the configuration in which the overlapping portions of the plurality of images are joined to generate a subject image, the subject image can be generated by the most suitable pixel value, without adding the pixel values of the plurality of pixels. As a result, it is possible to provide an X-ray imaging apparatus capable of generating a smooth subject image even in a case where a subject image is generated based on a plurality of images captured while changing the imaging position.

EMBODIMENTS FOR CARRYING OUT THE INVENTION

Hereinafter, some embodiments in which the present invention is embodied will be described with reference to the attached drawings.

With reference to FIGS. 1 to 11, the configuration of an X-ray imaging apparatus 100 according to one embodiment will be described.

(Configuration of X-Ray Imaging Apparatus)

Figure 1:
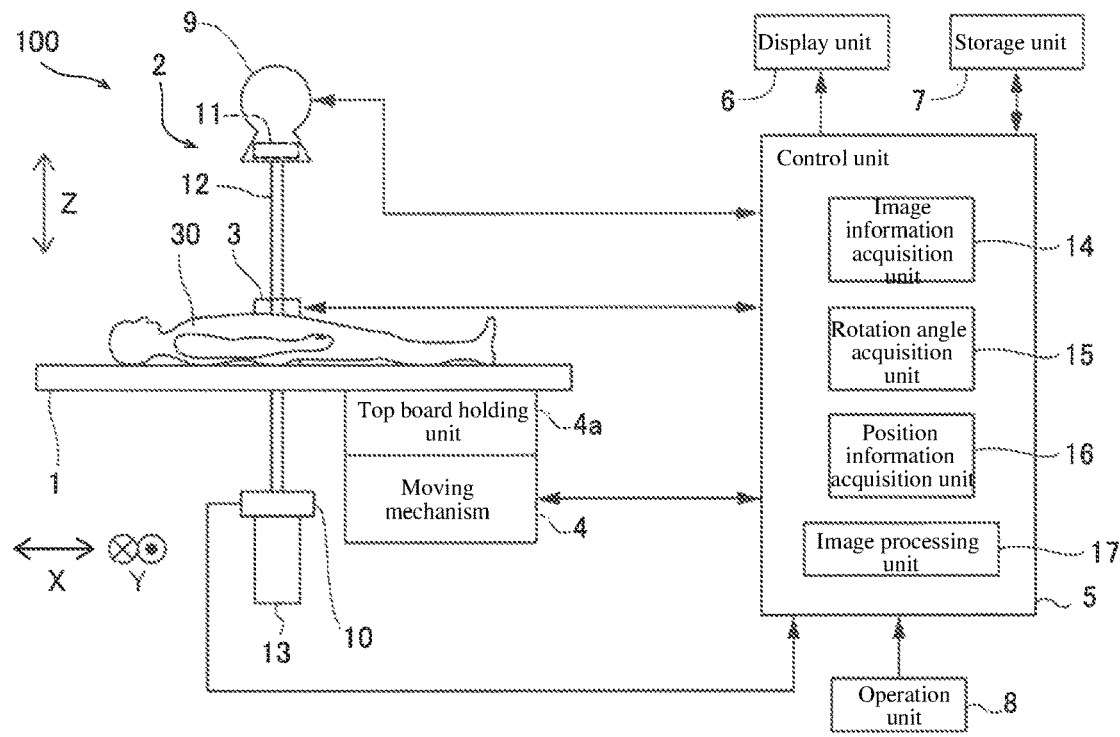
FIG. 1 is a schematic diagram showing an entire configuration of an X-ray imaging apparatus according to one embodiment.

As shown in FIG. 1, the X-ray imaging apparatus 100 according to this embodiment is provided with a top board 1, an imaging unit 2, a rotation mechanism 3, a moving mechanism 4, a control unit 5, a display unit 6, a storage unit 7, and an operation unit 8.

The top board 1 is configured to place a subject 30 thereon. The top board 1 is formed in a rectangular flat plate shape in a plan view. The subject 30 is placed on the top board 1 in such a manner that the head-foot direction of the subject 30 is oriented in the direction along the long side of the top board 1 and that the left-right direction of the subject 30 is oriented in the direction along the short side of the top board 1. In this specification, the long side direction of the top board 1 is defined as an X-direction. In addition, the short-side direction of the top board 1 is defined as a Y-direction. Further, the direction orthogonal to the X-direction and the Y-direction is defined as a Z-direction. The head-foot direction of the subject 30 means a direction along a straight line connecting the head and the foot of the subject 30.

The imaging unit 2 includes an X-ray source 9 and an X-ray detection unit 10. Further, the imaging unit 2 is configured to capture X-ray images (the X-ray image 40a, the X-ray image 40b, the X-ray image 40c, and the X-ray image 40d) (see FIG. 4). The X-ray source 9 is arranged on one side in the Z-direction with respect to the top board 1. The X-ray source 9 is configured to irradiate the subject 30 with X-rays when a voltage is applied by an X-ray tube drive unit (not shown). The X-ray source 9 is provided with a collimator 11 capable of adjusting the X-ray irradiation field, which is the irradiation range of X-rays. Further, as shown in FIG. 1, the X-ray source 9 is attached to the one side tip end of the C-shaped arm 12. Note that the X-ray image is one example of the "image" as recited in claims.

The X-ray detection unit 10 is configured to detect the X-rays emitted from the X-ray source 9 and transmitted through the subject 30. The X-ray detection unit 10 includes, for example, an FPD (Flat Panel Detector). The X-ray detection unit 10 is attached to the other side (opposite side with respect to the X-ray source 9) tip end of the C-shaped arm 12. Further, the C-shaped arm 12 is arranged such that the respective tip end portions are arranged at the positions crossing the top board 1. That is, the X-ray detection unit 10 is arranged on the other side (opposite side with respect to the X-ray source 9) of the top board 1 across the top board 1. Thus, the X-ray imaging apparatus 100 is configured to be capable of capturing an X-ray image by emitting X-rays from the X-ray source 9 with the subject 30 placed on the top board 1 and detecting the X-rays that have passed through the subject 30 with the X-ray detection unit 10. Further, the X-ray detection unit 10 is configured to be slidable in a direction (the Z-direction in FIG. 1) in which the slide unit 13 extends by the slide unit 13 attached to the tip end of the C-shaped arm 12.

The rotation mechanism 3 is configured to be capable of rotating the imaging unit 2 by rotating the C-shaped arm 12 under the control of the control unit 5. The rotation mechanism 3 includes a moving mechanism for moving the C-shaped arm 12 along the outer periphery of the C-shaped arm 12. The rotation mechanism 3 is configured to be capable of rotating the C-shaped arm 12 about the axis of the longitudinal direction (X-direction) of the top board 1 and about the axis of the short direction (Y-direction) of the top board 1. The rotation mechanism 3 includes, for example, a motor.

The moving mechanism 4 includes the top board 1 for placing a subject 30 thereon. Further, the moving mechanism 4 is provided with the C-shaped arm 12 for integrally holding the X-ray source 9 and the X-ray detection unit 10. The moving mechanism 4 is configured to move at least one of the top board 1 and the imaging unit 2 so as to change the relative position between the top board 1 and the imaging unit 2 under the control of the control unit 5. Specifically, the moving mechanism 4 is configured such that the relative position between the top board 1 and the imaging unit 2 can be changed by moving the top board 1 in one of the X-direction, the Y-direction, and the Z-direction. The moving mechanism 4 includes a linear motion mechanism movable in the X-direction, a linear motion mechanism movable in the Y-direction, and a linear motion mechanism movable in the Z-direction. Each linear motion mechanism includes a ball screw, a linear motor, or the like.

In this embodiment, the moving mechanism 4 is provided with a top board holding unit 4a for holding the top board 1 at least in a plane in a manually movable manner. Thus, in this embodiment, the top board 1 can be moved automatically by the moving mechanism 4 and can also be moved manually by an operator.

The control unit 5 is configured to control the rotation mechanism 3 to rotate the imaging unit 2. Further, the control unit 5 is configured to relatively move the top board 1 and the imaging unit 2 by controlling the moving mechanism 4. The control unit 5 is a computer configured to include a CPU (Central Processing Unit), a ROM (Read Only Memory), a RAM (Random Access Memory), and the like. Further, the control unit 5 is provided with an image information acquisition unit 14, a rotation angle acquisition unit 15, a position information acquisition unit 16, and an image processing unit 17. The control unit 5 is configured to function as the image information acquisition unit 14, the rotation angle acquisition unit 15, and the position information acquisition unit 16 by executing various programs stored in the storage unit 7. That is, the image information acquisition unit 14, the rotation angle acquisition unit 15, and the position information acquisition unit 16 are processing blocks of programs executed by the control unit 5.

Figure 2:
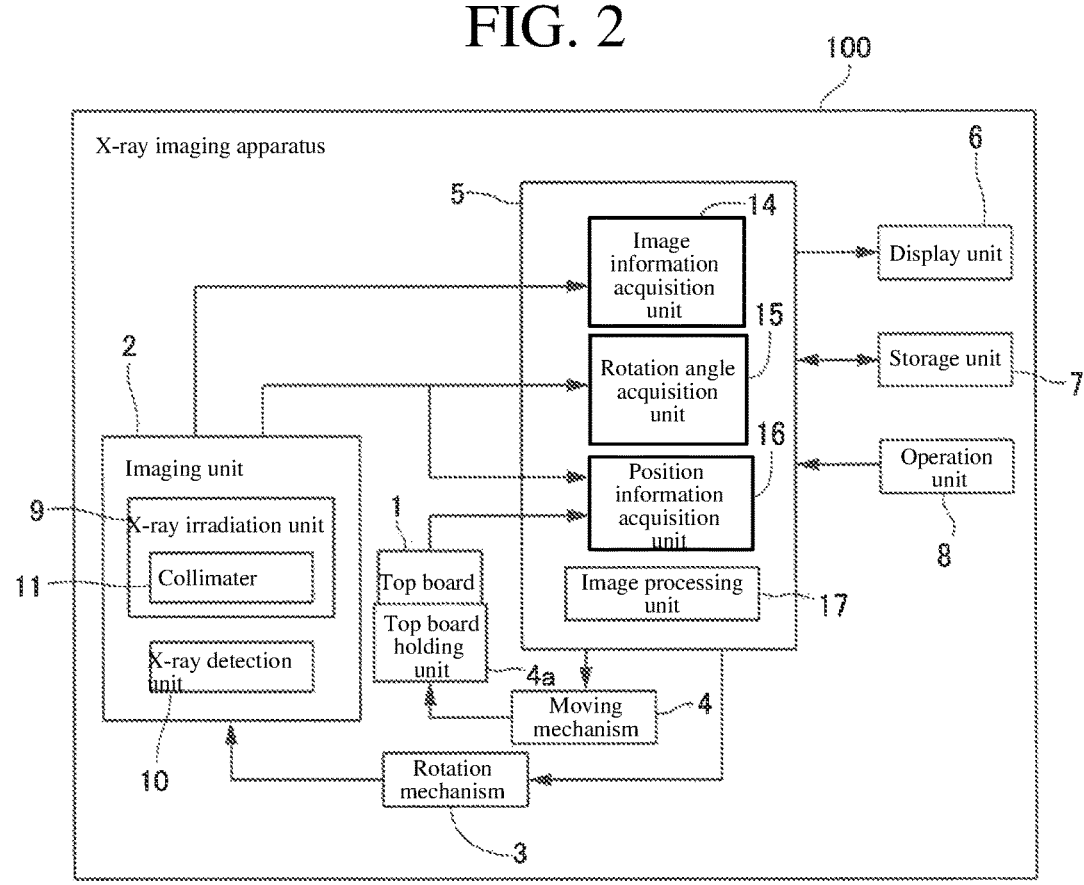
FIG. 2 is a block diagram showing the entire configuration of the X-ray imaging apparatus according to the embodiment.

As shown in FIG. 2, the image information acquisition unit 14 is configured to acquire the image information imaged by the imaging unit 2 from the X-ray detection unit 10. The image information acquired by the image information acquisition unit 14 is stored in the storage unit 7. The image information acquired by the image information acquisition unit 14 is used to generate the X-ray image by the image processing unit 17.

As shown in FIG. 2, the rotation angle acquisition unit 15 is configured to acquire the rotation angle 51 (see FIG. 8) of the imaging unit 2 rotated by the rotation mechanism 3. Note that the rotation angle 51 of the imaging unit 2 denotes the angle formed between the vertical direction and the optical axis 22 (see FIG. 8) of the X-rays.

As shown in FIG. 2, the position information acquisition unit 16 is configured to acquire the position information on the top board 1 moved by the moving mechanism 4. The position information on the top board 1 includes the coordinate information (X, Y, Z) at a predetermined position of the top board 1. For example, the position information on the top board 1 includes the coordinate information (X, Y, Z) at any position in the vicinity of the four corners of the top board 1. Thus, the position information acquisition unit 16 can acquire the body movement amount when the top board 1 is relatively moved by using the coordinate information on the top board 1 as the position information on the top board 1.

As shown in FIG. 2, the image processing unit 17 is configured to generate an X-ray image based on the image information acquired by the image information acquisition unit 14. Specifically, the image processing unit 17 is configured to acquire a plurality of X-ray images while changing the relative position by the moving mechanism 4 and generate a subject image 42 (see FIG. 4) based on a plurality of X-ray images (the X-ray image 40a, the X-ray image 40b, the X-ray image 40c, and the X-ray image 40d) (see FIG. 4). The image processing unit 17 includes, for example, a processor, such as, e.g., a GPU (Graphics Processing Unit) and an FPGA (Field-Programmable Gate Array) configured for image processing. The detailed configuration in which the image processing unit 17 generates the subject image 42 will be described later.

The display unit 6 is configured as, for example, a liquid crystal display. The display unit 6 is configured to display the X-ray image generated by the image processing unit 17 based on the image information captured by the imaging unit 2. The display unit 6 is configured to display the subject image 42 generated based on the X-ray image in the image processing unit 17.

The storage unit 7 includes, for example, an HDD (hard disk drive) or a nonvolatile memory. In the storage unit 7, programs used for processing the rotation mechanism 3, the moving mechanism 4, the image information acquisition unit 14, the rotation angle acquisition unit 15, the position information acquisition unit 16, and the image processing unit 17 are stored. The storage unit 7 is configured to be able to store the image information captured by the imaging unit 2, the rotation angle 51 of the imaging unit 2 acquired by the rotation angle acquisition unit 15, the position information on the top board 1 acquired by the position information acquisition unit 16, the X-ray image generated by the image processing unit 17, and the subject image 42 generated by the image processing unit 17. Note that the storage unit 7 may be wired or wirelessly connected to the X-ray imaging apparatus 100. Further, the storage unit 7 may be provided at a place away from the X-ray imaging apparatus 100 by being connected to the X-ray imaging apparatus 100 via a network.

The operation unit 8 includes, for example, a mouse and a keyboard. The operation unit 8 is configured to receive an input operation from an operator. The operation unit 8 is configured to transmit the received input operation to the control unit 5.

(Generation Method of Subject Image)

Next, referring to FIGS. 3 to 5, the configuration in which the image processing unit 17 generates the subject image 42 will be described.

Figure 3:
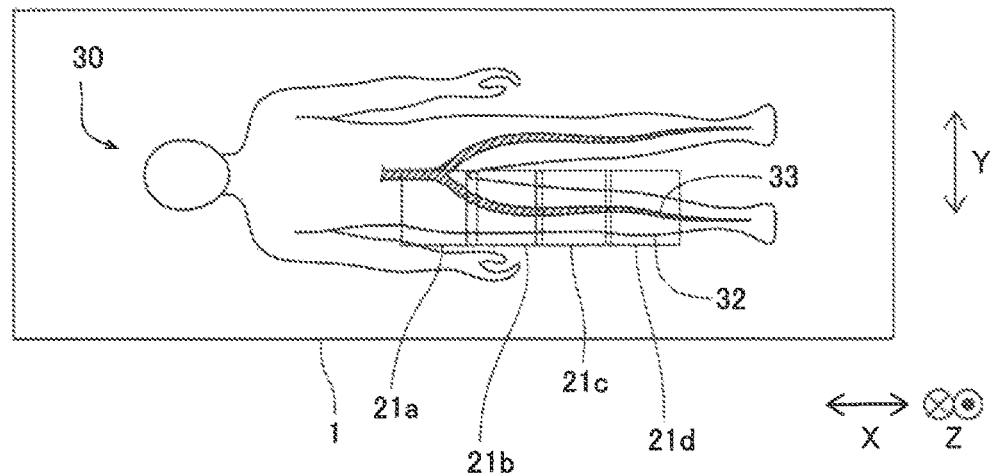
FIG. 3 is a schematic diagram for explaining imaging positions of a plurality of X-ray images.

The X-ray imaging apparatus 100 of this embodiment is configured to be able to perform X-ray imaging while moving the top board 1 by the moving mechanism 4 or manually moving the top board 1 at a plurality of imaging positions (the first imaging position 21a, the second imaging position 21b, the third imaging position 21c, and the fourth X-ray imaging 21d) of the subject 30 (see FIG. 3). Specifically, by moving the top board 1 in the X-direction and the Y-direction with respect to the imaging unit 2, as shown in FIG. 3, X-ray imaging is performed at a plurality of imaging positions. In this embodiment, the image information acquisition unit 14 acquires the image information captured by the X-ray imaging, and the position information acquisition unit 16 acquires the position information on the top board 1. In this embodiment, at least one X-ray image among the plurality of X-ray images (the X-ray image 40a, the X-ray image 40b, the X-ray image 40c, and the X-ray image 40d) (see FIG. 4) is an image in which the contrast agent administered to the inside of the subject 30 is reflected. Specifically, the X-ray image includes an image in which the blood vessel 33 of the lower limb portion 32 of the subject 30 is imaged. The subject image 42 also includes an X-ray image in which the blood vessel 33 of the lower limb portion 32 of the subject 30 is imaged.

In this embodiment, X-ray imaging is performed at a plurality of imaging positions. In FIG. 3, for the sake of convenience, an example is shown in which the X-ray imaging apparatus 100 captures X-ray images (the X-ray image 40a, the X-ray image 40b, the X-ray image 40c, and the X-ray image 40d) at four positions, i.e., the first imaging position 21a, the second imaging position 21b, the third imaging position 21c, and the fourth imaging position 21d, among the plurality of X-ray imaging positions where the X-ray imaging apparatus 100 captures images. Note that in this embodiment, a plurality of X-ray images is captured at a collection rate capable of suppressing the parallax caused by the movement of the same pixel between a plurality of X-ray images caused by the movement of the top board 1 to a degree difficult to be visually recognized. The collection rate is, for example, 7.5 fps (Frame Per Second).

Figure 4:
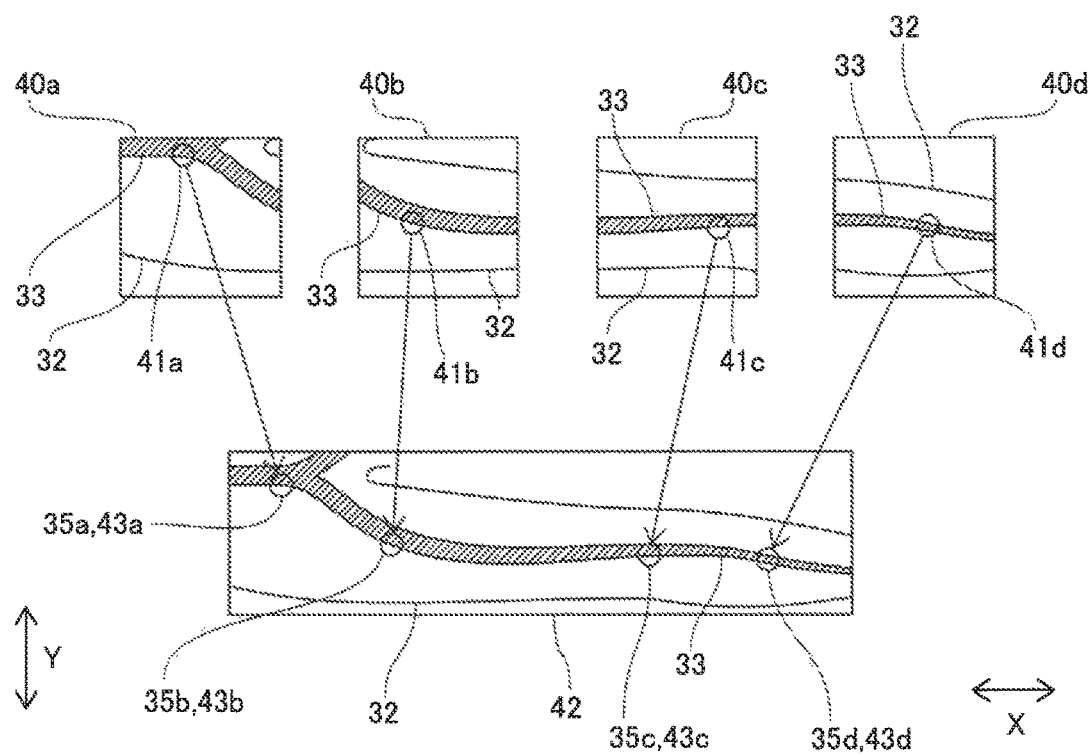
FIG. 4 is a schematic diagram for explaining the configuration for generating a subject image based on a plurality of X-ray images.

As shown in FIG. 4, the image processing unit 17 generates X-ray images captured at a plurality of imaging positions from the image information captured by X-ray imaging. In the example shown in FIG. 4, the image processing unit 17 generates the X-ray image 40a, the X-ray image 40b, the X-ray image 40c, and the X-ray image 40d captured at each of the first imaging position 21a to the fourth imaging position 21d. The image processing unit 17 is configured to set a reference plane 34 (see FIG. 6) that is an imaging region used when generating a subject image 42, based on the plurality of X-ray images. Further, the image processing unit 17 is configured to generate a subject image 42 on the reference plane 34 by determining each of the pixel values of the plurality of pixel corresponding points (the pixel corresponding point 35a, the pixel corresponding point 35b, the pixel corresponding point 35c, and the pixel corresponding point 35d) included in the reference plane 34, based on the X-ray images. In this embodiment, it is configured to generate a subject image 42 on the reference plane 34 by determining based on the plurality of X-ray images. In other words, each pixel corresponding point (the pixel corresponding point 35a, the pixel corresponding point 35b, the pixel corresponding point 35c, and the pixel corresponding point 35d) on the reference plane 34 is each pixel (the pixel 43a, the pixel 43b, the pixel 43c, and the pixel 43d) of the subject image 42.

In the example shown in FIG. 4, for convenience, an example is shown in which the pixel corresponding point 35a, the pixel corresponding point 35b, the pixel corresponding point 35c, and the pixel corresponding point 35d on the reference plane 34 (the pixel 43a, the pixel 43b, the pixel 43c, and the pixel 43d of the subject image 42) are selected. In the case where the X-ray image in which the pixel corresponding to the pixel corresponding point is reflected is one, the image processing unit 17 generates the subject image 42 by selecting the pixel value of the pixel of the X-ray image in which the pixel corresponding point is reflected. Specifically, as shown in FIG. 4, the image processing unit 17 selects the pixel value of each pixel (the pixel 41a, the pixel 41b, the pixel 41c, and the pixel 41d) corresponding to each pixel corresponding point (the pixel corresponding point 35a, the pixel corresponding point 35b, the pixel corresponding point 35c, and the pixel corresponding point 35d) on the reference plane 34 to generate the subject image 42.

Further, in a case where there is a plurality of X-ray images in which the pixels corresponding the image corresponding points are reflected, the image processing unit 17 is configured to select the pixel value corresponding to the pixel corresponding point in the X-ray image in which the pixel corresponding the pixel corresponding point is most clearly reflected, among the plurality of X-ray images (the X-ray image 40a, the X-ray image 40b, the X-ray image 40c, and the X-ray image 40d) to determine the pixel value of the pixel corresponding point. Note that the "pixel corresponding to the pixel corresponding point is most clearly reflected" means that the difference (contrast) between the pixel value of the pixel corresponding to the pixel corresponding point and the pixel value of the background portion is the largest.

(In a Case Where There is a Plurality of X-Ray Images in which Point in a Reference Plane is Reflected)

Next, referring to FIG. 5, in a case where there is a plurality of X-ray images in which the pixel corresponding points on the reference plane 34, which of the pixel value of the pixel included in the plurality of X-ray images is to be selected as the pixel value of the pixel corresponding point on the reference plane 34 will be described.

Figure 5:
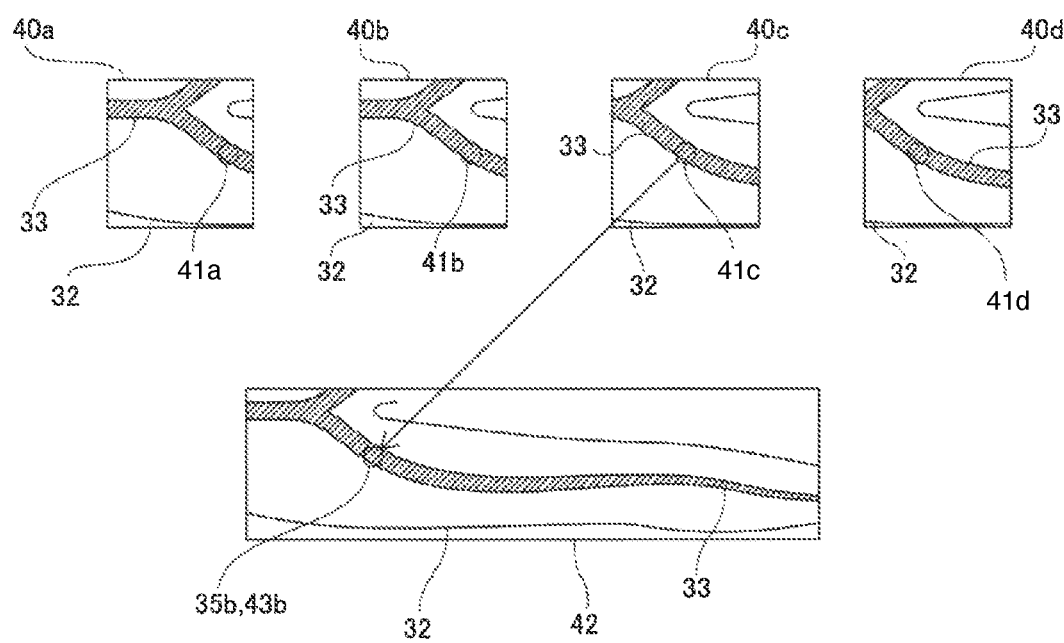
FIG. 5 is a schematic diagram for explaining which pixel is to be selected as a pixel for determining a pixel value of a pixel corresponding point on the reference plane in a case where the same pixel is contained in a plurality of X-ray images.

As shown in FIG. 5, the X-ray images 40a, 40b, 40c, and 40d each include a pixel corresponding to the pixel corresponding point 35b (the pixel 43b of the subject image 42) on the reference plane 34. In each of the X-ray images (the X-ray images 40a to 40d), the pixel 41a, the pixel 41b, the pixel 41c, and the pixel 41d are pixels each corresponding to the pixel corresponding point 35b on the reference plane 34.

In this embodiment, in a case where there is a plurality of X-ray images in which the pixel corresponding points are reflected, the image processing unit 17 is configured to select the pixel value of the pixel at the position closest to the center of the X-ray image as the pixel in which the pixel corresponding point is most clearly reflected among the pixels corresponding to the pixel corresponding points on the reference plane 34 in the plurality of pixel images to determine the pixel value of the pixel corresponding point. Note that the pixel at the position of the center of the X-ray image is a pixel to which the X-rays are incident to the pixel corresponding point on the reference plane 34 at the incident angle of 90 degrees. Therefore, the closer to the center position of the X-ray image the pixel is, the less the image blur due to the incident of the X-rays from the oblique direction is. Therefore, the pixel corresponding to the pixel corresponding point in the X-ray image becomes the clearest.

(Reference Plane)

Figure 6:
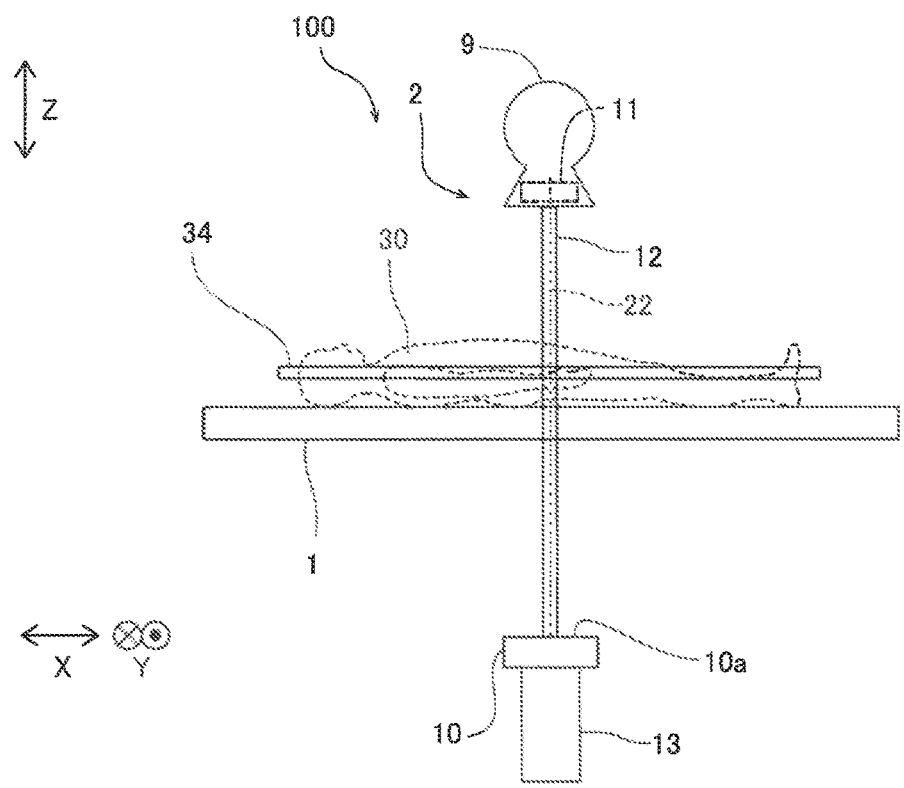
FIG. 6 is a schematic diagram for explaining a reference plane when a detection surface of an X-ray detection unit is arranged to be parallel to a top board.
Figure 7:
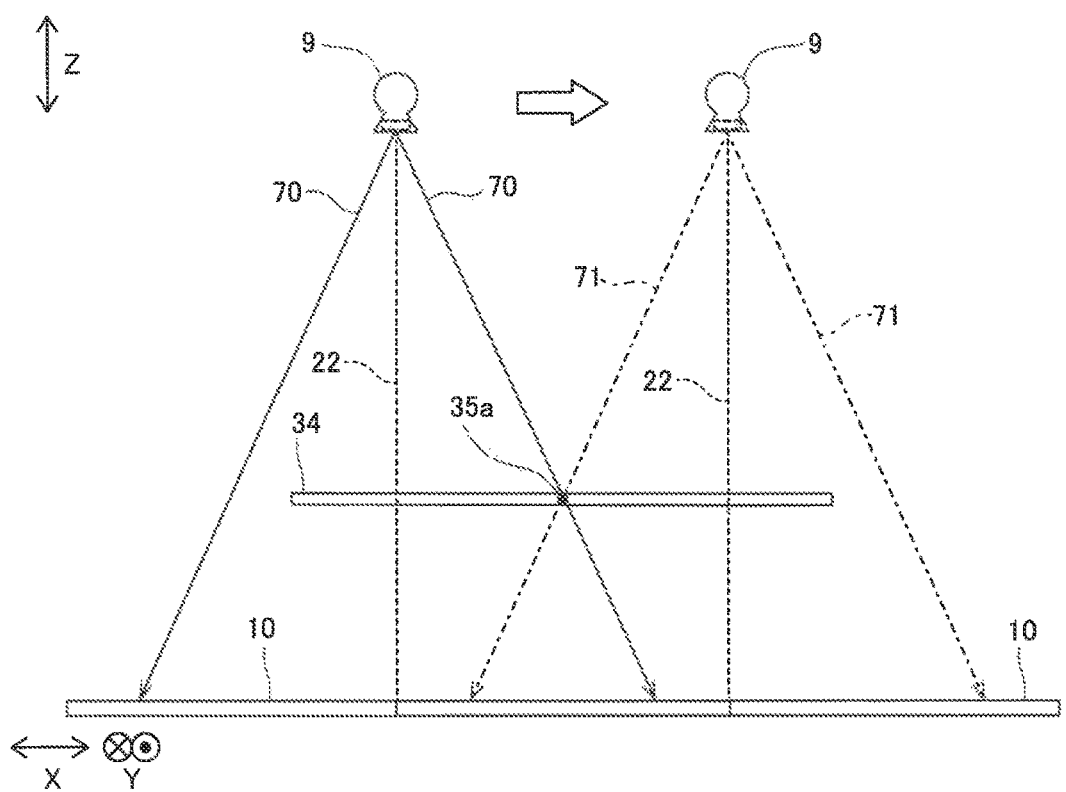
FIG. 7 is a schematic diagram for explaining that the incident angle of X-rays to the same pixel corresponding point varies due to the relative movement between the imaging unit and the top board.
Figure 8:
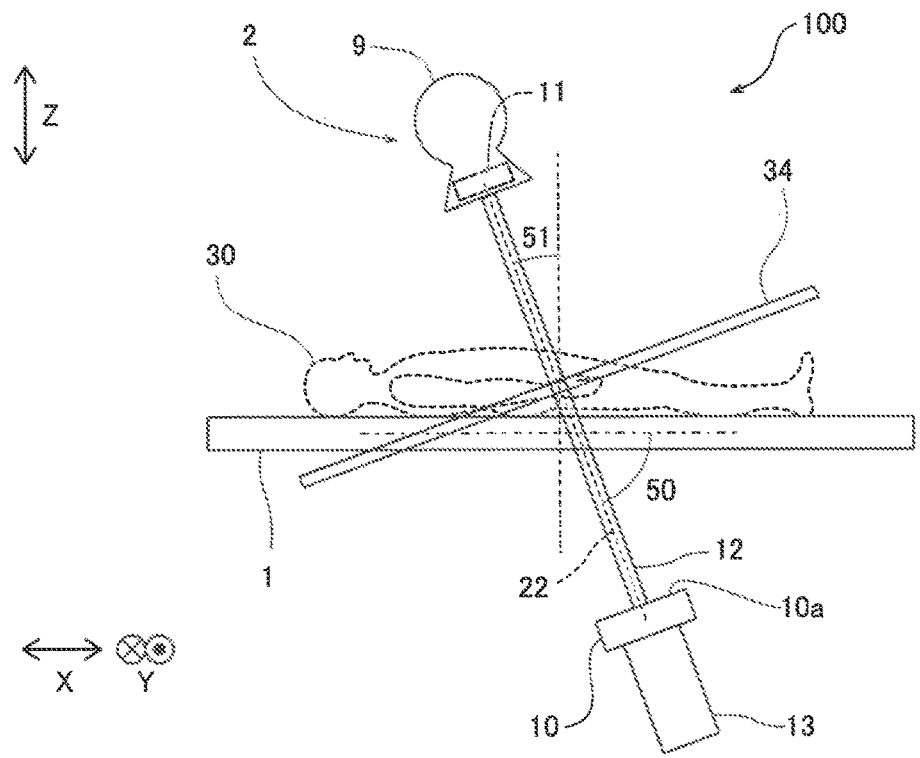
FIG. 8 is a schematic diagram for explaining the reference plane when the detection surface of the X-ray detection unit is placed in a state of being inclined with respect to the top board.
Figure 9:
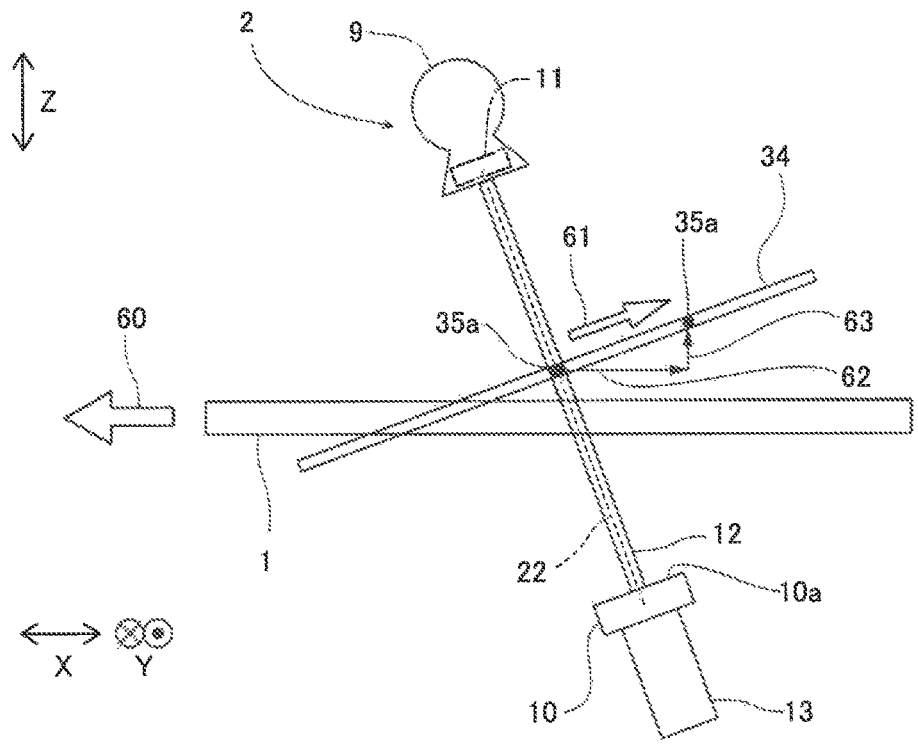
FIG. 9 is a schematic diagram for explaining the direction in which the pixel corresponding point on the reference plane moves when the top board is moved in a state in which the imaging unit is inclined with respect to the top board.

Next, referring to FIGS. 6 to 9, the reference plane 34 will be described. Note that FIGS. 6 and 7 show an example in which the detection surface 10a of the X-ray detection unit 10 is arranged to be parallel to the top board 1. Further, FIGS. 8 and 9 show an example in which the detection surface 10a of the X-ray detection unit 10 is arranged in a state of being inclined with respect to the top board 1.

(In a Case Where Imaging Unit is Arranged in Parallel To Top Board)

First, referring to FIGS. 6 and 7, the reference plane 34 in a case where the detection surface 10a of the X-ray detection unit 10 is arranged to be parallel to the top board 1 will be explained.

As shown in FIG. 6, the reference plane 34 is a plane along the detection surface 10a of the X-ray detection unit 10. Further, the reference plane 34 is a flat plane. Note that the plane along the detection surface 10a of the X-ray detection unit 10 denotes a plane parallel to the detection surface 10a of the X-ray detection unit 10. The reference plane 34 is an imaging region when generating a subject image 42 based on a plurality of X-ray images and is set based on the respective sizes of the plurality of X-ray images. Further, the reference plane 34 determines the height of the region to be imaged by setting the height position from the top board 1. The height position is set to any position by a user. For example, the height position is set by a user to a position, such as +10 cm with reference to the isocenter, which is a point where the irradiated X-rays are concentrated.

Here, as shown in FIG. 7, the X-rays emitted from the X-ray source 9 are emitted in a radially spread manner until they reach the X-ray detection unit 10. Note that in the example shown in FIG. 7, the X-rays emitted at the first imaging position 21a (see FIG. 3) are illustrated by solid lines 70. Further, the X-rays emitted at the second imaging position 21b (see FIG. 3) are illustrated by one-dot chain lines 71. Further, the optical axis 22 of each X-ray is illustrated by a broken line. When imaging is performed while moving the imaging unit 2, in some cases, the X-rays emitted from different imaging positions may be incident on the same pixel corresponding point 35a on the reference plane 34.

As shown in FIG. 7, in a case where the X-rays (see the solid lines 70) emitted from the first imaging position 21a and the X-rays (see the one-dot chain lines 71) emitted from the second imaging position 21b are incident on the same pixel corresponding point 35a on the reference plane 34, the incident angles of the X-rays differ. In this case, in the X-ray image based on one of the X-rays, it becomes a state of looking up the pixel corresponding point 35a, while in the X-ray image based on the other of the X-rays, it becomes the state of looking down the pixel corresponding point 35a. Therefore, when these X-ray images are connected, the connected portion becomes unnatural, thereby deteriorating the image quality of the subject image 42. Thus, in this embodiment, the image processing unit 17 is configured to generate a subject image 42 by selecting the pixel value of the pixel corresponding point 35a on the reference plane 34 as the pixel value of the pixel of the X-ray image. Note that the "state of looking up the pixel corresponding point 35a" means a state in which the pixel corresponding point 35a is located on the traveling direction side with respect to the optical axis 22 of the X-rays. Further, the "state of looking down the pixel corresponding point" means a state in which the pixel corresponding point 35a is located on a side opposite to the traveling direction side with respect to the optical axis 22 of the X-rays. That is, in the example of FIG. 7, the X-ray image based on the X-rays emitted at the first imaging position 21a becomes a state of looking up the pixel corresponding point 35a. Further, the X-ray image based on the X-rays emitted at the second imaging position 21b becomes a state of looking down the pixel corresponding point 35a. Further, the example shown in FIG. 7 has been described with reference to the pixel corresponding point 35a, but the same can be applied to other pixel corresponding points.

(In a Case Where Imaging Unit is Arranged in a State of being Inclined to Top Board)

Next, referring to FIGS. 8 and 9, the reference plane 34 in a case where the detection surface 10a of the X-ray detection unit 10 is in a state of being inclined with respect to the top board 1 will be described.

FIG. 8 shows an example in which the imaging unit 2 is inclined with respect to the top board 1 by rotating the imaging unit 2 about the Y-direction by the rotation mechanism 3 (see FIG. 6). As shown in FIG. 8, the rotation mechanism 3 is configured to be capable of attaining a state in which the angle 50 formed between the optical axis 22 of the X-rays emitted from the X-ray source 9 and the longitudinal direction (the X-direction) of the top board 1 is inclined by rotating the imaging unit 2 from the vertical direction by the rotation angle 51. That is, when the rotation angle 50 formed between the optical axis of the X-rays and the longitudinal direction (the X-direction) of the top board 1 and the rotation angle 51 of the imaging unit 2 are added, it becomes 90 degrees. Therefore, when either one of the rotation angle 51 of the imaging unit 2 and the angle 50 formed between the optical axis 22 of the X-rays and the longitudinal direction of the top board 1 (the X-direction) is increased, the other is reduced. Note that the "state in which the angle 50 formed between the optical axis 22 of the X-rays emitted from the X-ray source 9 and the longitudinal direction (the X-direction) of the top board 1 is inclined" means a state in which the angle 50 formed between the optical axis 22 of the X-rays emitted from the X-ray source 9 and the longitudinal direction (the X-direction) of the top board 1 becomes an angle excluding 0 degrees, 90 degrees, and 180 degrees in the angle range from 0 degrees to 180 degrees.

As shown in FIG. 8, even in a case where the imaging unit 2 is inclined with respect to the top board 1, the reference plane 34 is a plane along the detection surface 10a of the X-ray detection unit 10 and a flat plane. Further, as shown in FIG. 8, the reference plane 34 becomes an inclined state with respect to the top board 1.

Here, as shown in FIG. 9, when the top board 1 is moved along the direction of the arrow 60 in a state in which the imaging unit 2 is inclined with respect to the top board 1, the pixel corresponding point 35a on the reference plane 34 moves in the direction along the arrow 61. The direction along the arrow 61 can be decomposed into the X-direction and the Z-direction as shown by the arrows 62 and 63. That is, in a case where the top board 1 is moved in the X-direction in a state in which the imaging unit 2 is inclined with respect to the top board 1, the pixel corresponding point 35a on the reference plane 34 is moved in the Z-direction in addition to the X-direction. The movement in the Z-direction also causes the movement of the X-rays in the direction of the optical axis 22, thereby causing the change in the magnification ratio in the X-ray image. Therefore, in a case where imaging is performed in a state in which the imaging unit 2 is inclined with respect to the top board 1, the X-ray images (the X-ray image 40a, the X-ray image 40b, the X-ray image 40c, and the X-ray image 40d) become images different from each other in the magnification ratio. Note that although the example shown in FIG. 9 has been described using the pixel corresponding point 35a, the same can be applied to other pixel corresponding points.

Therefore, in this embodiment, in a case where the imaging unit 2 is arranged in a state of being inclined with respect to the top board 1, the reference plane 34 is set such that the magnification ratios of the plurality of X-ray images become constant, respectively. In other words, in this embodiment, the image processing unit 17 is configured to change the magnification ratio of each of the plurality of X-ray images such that the subject 30 reflected in each X-ray image (the X-ray image 40a, the X-ray image 40b, the X-ray image 40c, and the X-ray image 40d) becomes the same size and then select the pixel value of each pixel corresponding point on the reference plane 34 from the plurality of X-ray images.

(Coordinate Transformation of X-Ray Image)

Next, referring to FIGS. 10 and 11, the configuration in which the image processing unit 17 performs the coordinate transformation of the X-ray image will be described.

Figure 10:
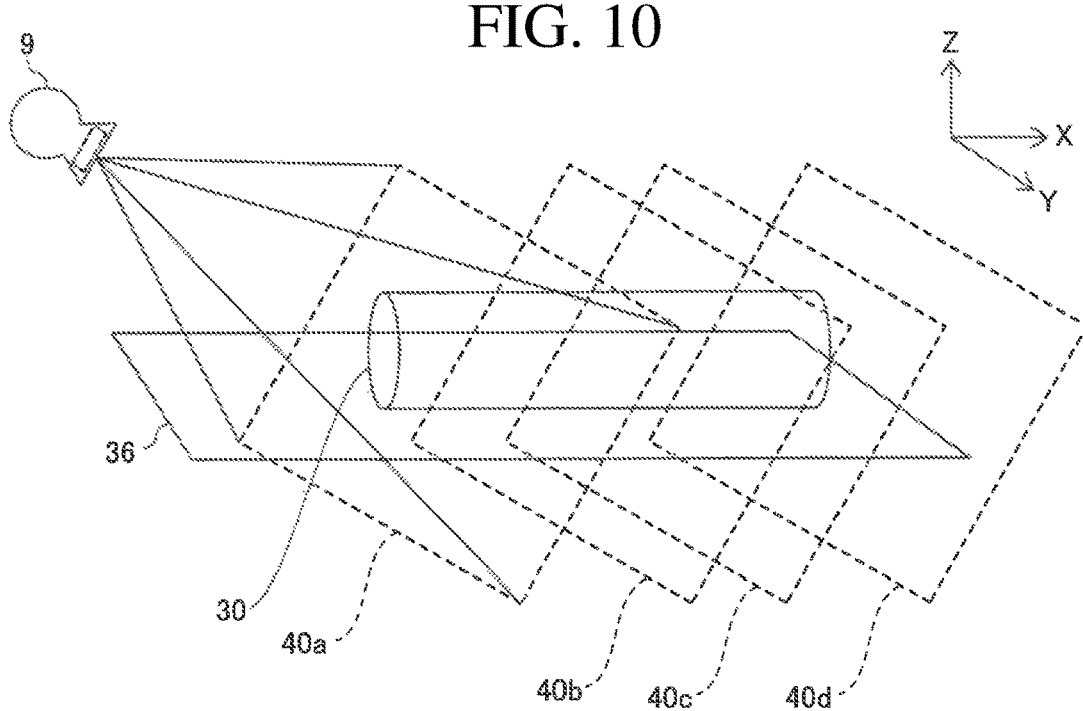
FIG. 10 is a schematic diagram for explaining a plurality of images captured in a top board coordinate system.

The example shown in FIG. 10 shows a top board coordinate system (XYZ coordinate system). The top board coordinate system is a coordinate system in which the XY plane is a plane 36 parallel to the top board 1 and the direction perpendicular to the XY plane is the Z-direction. The relative position between the top board 1 and the imaging unit 2 is managed by the top board coordinate system. The top board coordinate system is invariant in the direction of each coordinate axis of XYZ in the X-ray imaging apparatus 100.

Figure 11:
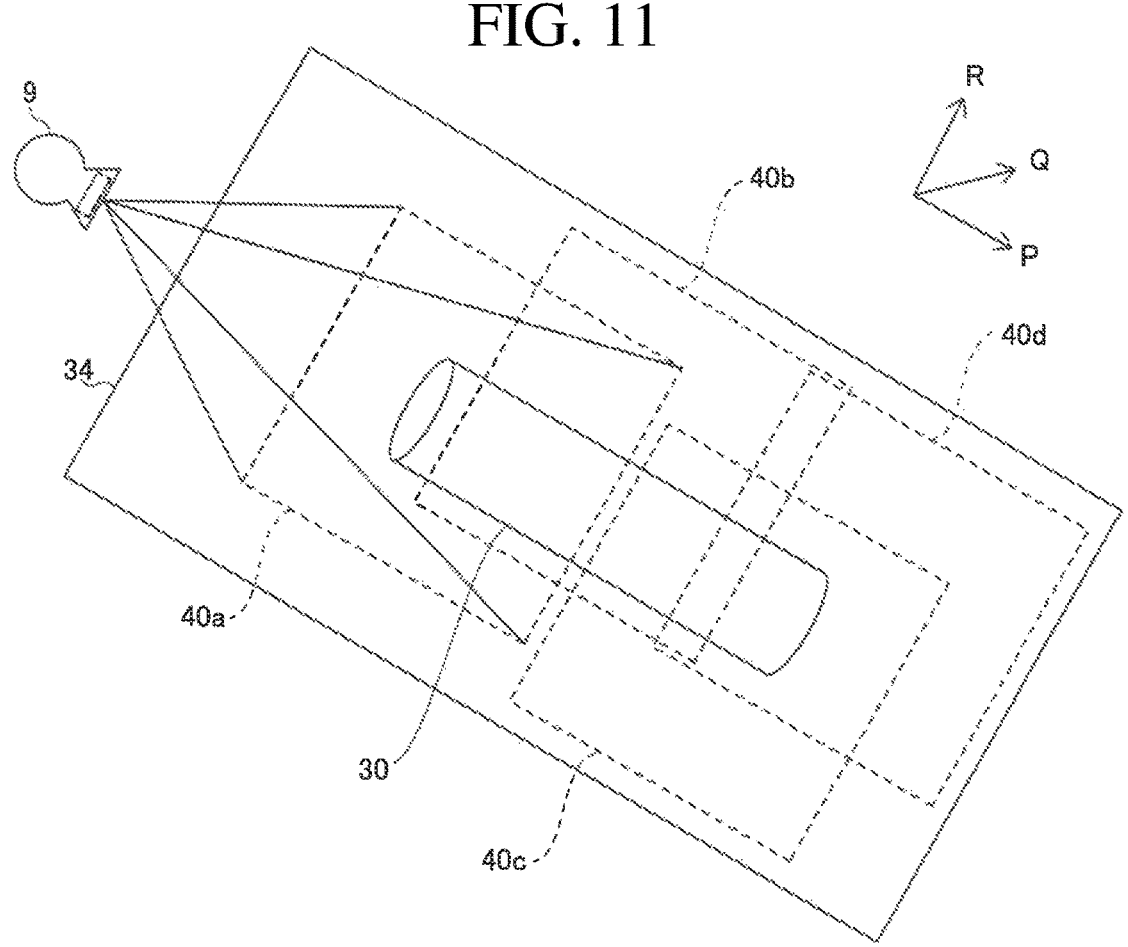
FIG. 11 is a schematic diagram for explaining the configuration for converting the coordinate of each of the pixels of the plurality of images into a three-dimensional coordinate.

The example shown in FIG. 11 shows a three-dimensional coordinate system (PQR coordinate system). In the three-dimensional coordinate system, the RP plane is a plane of an image when generating an X-ray image, and the the Q-direction is the depth-direction. In other words, the RP plane is a plane along the detection surface 10a of the X-ray detection unit 10, i.e., the reference plane 34, and the Q direction is the direction of the optical axis 22 of the X-rays. The three-dimensional coordinate system is a coordinate system (camera coordinate system) for defining the reference plane 34, and the direction of the respective coordinate axes of PQR can be arbitrarily changed according to the reference plane 34. In this embodiment, since the reference plane 34 is parallel to the detection surface 10a, the three-dimensional coordinate system is set according to the orientation of the X-ray detection unit 10 (the angle of the C-shaped arm 12). Whether the X-rays transmitted through which of the pixel corresponding point of the reference plane 34 were detected by which of the pixel of the X-ray image is determined by the coordinate transformation between the top board coordinate system and the three-dimensional coordinate system.

In this embodiment, the image processing unit 17 converts the coordinate of the pixels of the plurality of X-ray images from the top board coordinate system (XYZ coordinate system) to the three-dimensional coordinate system (PQR coordinate system). The image processing unit 17 converts the coordinate of the top board coordinate system to the three-dimensional coordinate system by a matrix transformation, based on, for example, the angle of the C-shaped arm 12 when each X-ray image is captured and the position information on the top board 1. Note that the Q coordinate after the coordinate transformation is a coordinate in the direction of the optical axis 22 of the X-rays. Therefore, in the image processing unit 17, the Q coordinate of each X-ray image after the coordinate transformation is constant, and therefore, the magnification ratio of each X-ray image is constant.

In a case where imaging is performed in a state in which the imaging unit 2 is not inclined with respect to the top board 1 (see FIG. 6), no change in the magnification ratio occurs in the X-ray images (the X-ray image 40a, the X-ray image 40b, the X-ray image 40c, and the X-ray image 40d) captured at the plurality of imaging positions (the first imaging position 21a, the second imaging position 21b, the third imaging position 21c, and the fourth imaging position 21d). However, in the subject 30, when the X-ray irradiation angle is 90 degrees, the points having the same X and Y coordinates and different Z coordinates are reflected at the same position on the X-Y plane, but when the X-rays are emitted from an oblique direction, the above-described points are reflected at different positions on the X-Y plane. Therefore, even in a state in which the imaging unit 2 is not inclined with respect to the top board 1, the image processing unit 17 performs the coordinate transformation of the X-ray image in order to acquire all of the X-ray images in which the pixels corresponding to the pixel corresponding points are reflected, when selecting the pixel for determining the pixel value of the pixel corresponding point on the reference plane 34. In this embodiment, the image processing unit 17 performs the coordinate transformation for each pixel of the plurality of X-ray images.

Figure 12:
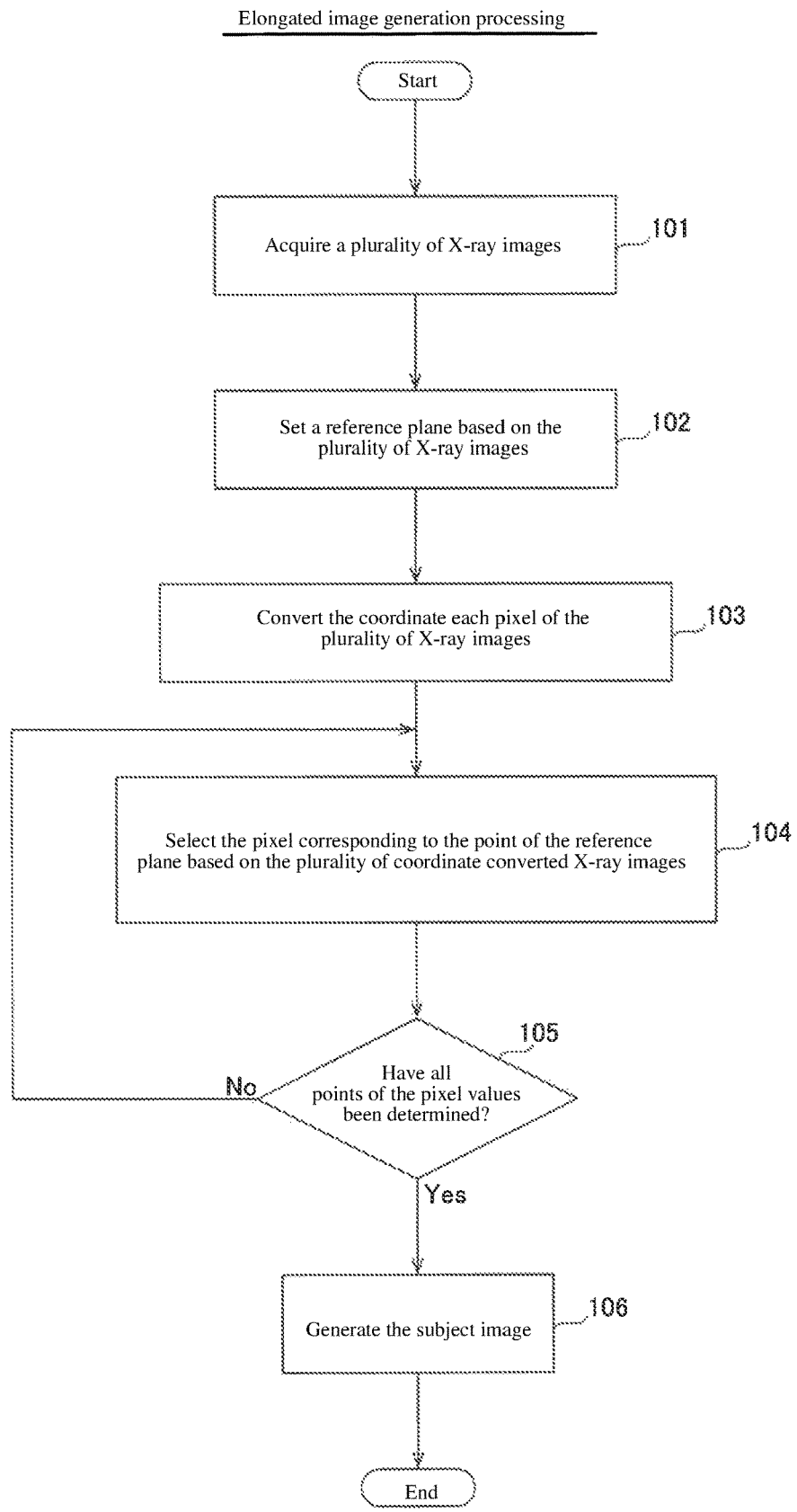
FIG. 12 is a flowchart for explaining the generation processing of a subject image in the X-ray imaging apparatus according to one embodiment.

Next, referring to FIG. 12, the processing in which the X-ray imaging apparatus 100 of this embodiment generates the subject image 42 will be described.

In Step 101, the image processing unit 17 acquires X-ray images (the X-ray image 40a, the X-ray image 40b, the X-ray image 40c, and the X-ray image 40d) captured at a plurality of imaging positions (the first imaging position 21a, the second imaging position 21b, the third imaging position 21c, and the fourth imaging position 21d) while moving the top board 1.

Next, in Step 102, the image processing unit 17 sets a reference plane 34 based on the plurality of X-ray images.

Next, in Step 103, the image processing unit 17 converts the coordinate of each pixel (the pixel 41a, the pixel 41b, the pixel 41c, and the pixel 41d) of the plurality of X-ray images. Note that the reference plane 34 is set such that the magnification ratio of each X-ray image becomes constant. Therefore, when the X-ray image captured at each imaging position is subjected to the coordinate transformation on the reference plane 34 of the three-dimensional coordinate system, the magnification ratios of the respective X-ray images are aligned to be constant as a result.

Next, in Step 104, the image processing unit 17 selects the pixel corresponding to each pixel corresponding point on the reference plane 34 based on the plurality of X-ray images after the coordinate transformation and determines the pixel value at each pixel corresponding point.

Next, in Step 105, the image processing unit 17 determines whether or not the pixel values at all of the pixel corresponding points on the reference plane 34 have been determined. When the pixel values of all of the pixel corresponding points on the reference plane 34 have been determined, the processing proceeds to Step 106. When the pixel values of all of the pixel corresponding points on the reference plane 34 have not been determined, the processing returns to Step 104.

In Step 106, the image processing unit 17 generates a subject image 42. Thereafter, the processing ends.

Effects of this Embodiment

In this embodiment, the following effects can be obtained.

In this embodiment, as described above, the apparatus is provided with the imaging unit 2 for capturing an X-ray image, the imaging unit including the X-ray source 9 for irradiating the subject 30 with X-rays and the X-ray detection unit 10 for detecting the X-rays transmitted through the subject 30. The apparatus is further provided with the moving mechanism 4 including the top board 1 for placing the subject 30 thereon, the moving mechanism 4 being capable of moving at least one of the top board 1 and the imaging unit 2 to change the relative position between the top board 1 and the imaging unit 2. The apparatus is further provided with the image processing unit 17 for acquiring a plurality of X-ray images (the X-ray image 40*a*, the X-ray image 40*b*, the X-ray image 40*c*, and the X-ray image 40*d*) while changing the relative position by the moving mechanism 4 and generating the subject image 42 based on the plurality of X-ray images. The image processing unit 17 is configured to generate the subject image 42 on the reference plane 34 by setting the reference plane 34 that is an imaging region when generating the subject image 42 based on the plurality of subject images based on the plurality of X-ray images and determining each pixel value of the plurality of pixel corresponding points included in the reference plane 34. Further, in a case where there is a plurality of X-ray images in which the pixel corresponding points are reflected, the image processing unit 17 is configured to select the pixel corresponding to the pixel corresponding point in the image in which the pixel corresponding point is most clearly reflected among the plurality of images and determine the pixel value of the pixel corresponding point.

By configuring as described above, the pixel value on each pixel corresponding point (the pixel corresponding point 35*a*, the pixel corresponding point 35*b*, the pixel corresponding point 35*c*, and the pixel corresponding point 35*d*) on the reference plane 34 is selected from the pixel corresponding to the pixel corresponding point in the image in which the pixel corresponding point is most clearly reflected, among the plurality of X-ray images (the X-ray image 40*a*, the X-ray image 40*b*, the X-ray image 40*c*, and the X-ray image 40*d*). Thus, a subject image 42 can be generated based on the pixel value selected from one pixel corresponding to each pixel corresponding point of the reference plane 34. Therefore, unlike the configuration in which the overlapping portions of the plurality of X-ray images are connected to generate the subject image 42, the subject image 42 can be generated by the pixel value of the most suitable pixel, without adding the pixel values of a plurality of pixels. As a result, even in a case where the subject image 42 is generated based on a plurality of X-ray images captured while changing the imaging position, an X-ray imaging apparatus 100 capable of generating a smooth subject image 42 can be provided.

Further, in this embodiment, as described above, in a case where there is a plurality of X-ray images in which the pixel corresponding points are reflected, the image processing unit 17 is configured to determine the pixel value of the pixel corresponding point by selecting the pixel value of the pixel at the position closest to the center of the X-ray image as the pixel in which the pixel corresponding point is most clearly reflected, among the pixels corresponding to the pixel corresponding points on the reference plane 34 in the plurality of X-ray images (the X-ray image 40*a*, the X-ray image 40*b*, the X-ray image 40*c*, and the X-ray image 40*d*). Thus, in the X-ray image, the pixel at the position with less distortion can be selected as a pixel corresponding to each pixel corresponding point (the pixel corresponding point 35*a*, the pixel corresponding point 35*b*, the pixel corresponding point 35*c*, and the pixel corresponding point 35*d*). Consequently, a smooth subject image 42 can be easily generated.

Further, in this embodiment, as described above, the reference plane 34 is a plane along the detection surface 10*a* of the X-ray detection unit 10. Thus, for example, even in a case where a doctor or the like performs imaging in a state in which the imaging unit 2 is inclined, it is possible to generate a subject image 42 along the intended plane. As a result, the flexibility of the arrangement of the imaging unit 2 at the time of imaging the subject 30 can be improved, which in turn can improve the convenience of a user.

Further, in this embodiment, the reference plane 34 is a flat plane as described above. As a result, the subject image 42 can be generated as a planar image along a plane to be confirmed by a doctor or the like.

Further, in this embodiment, as described above, the moving mechanism 4 is further provided with the top board holding unit 4*a* for holding the top board 1 in a manually movable manner at least in a plane. Thus, unlike the configuration in which the top board 1 is moved automatically, it is possible to move the top board 1 at any rate. As a result, for example, when a doctor or the like performs imaging by moving the top board 1 while following a blood flow (the blood flow that differs in the flow rate depending on the subject 30) of a blood vessel 33 of a lower limb portion 32, it is possible to move the top board 1 at a speed corresponding to the blood flow rate, which differs individually, for each subject 30.

Further, in this embodiment, as described above, the moving mechanism 4 is further provided with the C-shaped arm 12 for integrally holding the X-ray source 9 and the X-ray detection unit 10. Thus, by changing the angle of the C-shaped arm 12, it is possible to perform imaging in a state in which the imaging unit 2 (the X-ray source 9 and the X-ray detection unit 10) is inclined with respect to the top board 1. Consequently, for example, even in a case where a blood vessel 33 to be observed is positioned below a bone or the like, it is possible to grasp the blood vessel 33 in the subject image 42 by capturing the image from an oblique direction.

Modified Embodiment

Note that it should be understood that the embodiments disclosed here are examples in all respects and are not restrictive. The scope of the present invention is indicated by the appended claims rather than by the description of the above-described embodiments and includes all modifications (changes) within the meanings and the scopes equivalent to the claims.

(First Modification)

For example, in the above-described embodiment, an example is shown in which in a case where there is a plurality of X-ray images in which the pixel corresponding points are reflected, the image processing unit 17 is configured to select the pixel value of the pixel at a position closest to the center of the X-ray image as the pixel value of the pixel corresponding point on the reference plane 34, but the present invention is not limited thereto. For example, as shown in FIG. 13, in a case where there is a plurality of X-ray images in which the pixel corresponding points are reflected, the image processing unit 17 may be configured to select the pixel value of the pixel with the highest concentration of the contrast agent as the pixel in which the pixel corresponding point is most clearly reflected, among the pixels corresponding to the pixel corresponding points in the plurality of X-ray images (the X-ray images 40a, the X-ray image 40b, the X-ray image 40c, and the X-ray image 40d).

Figure 13:
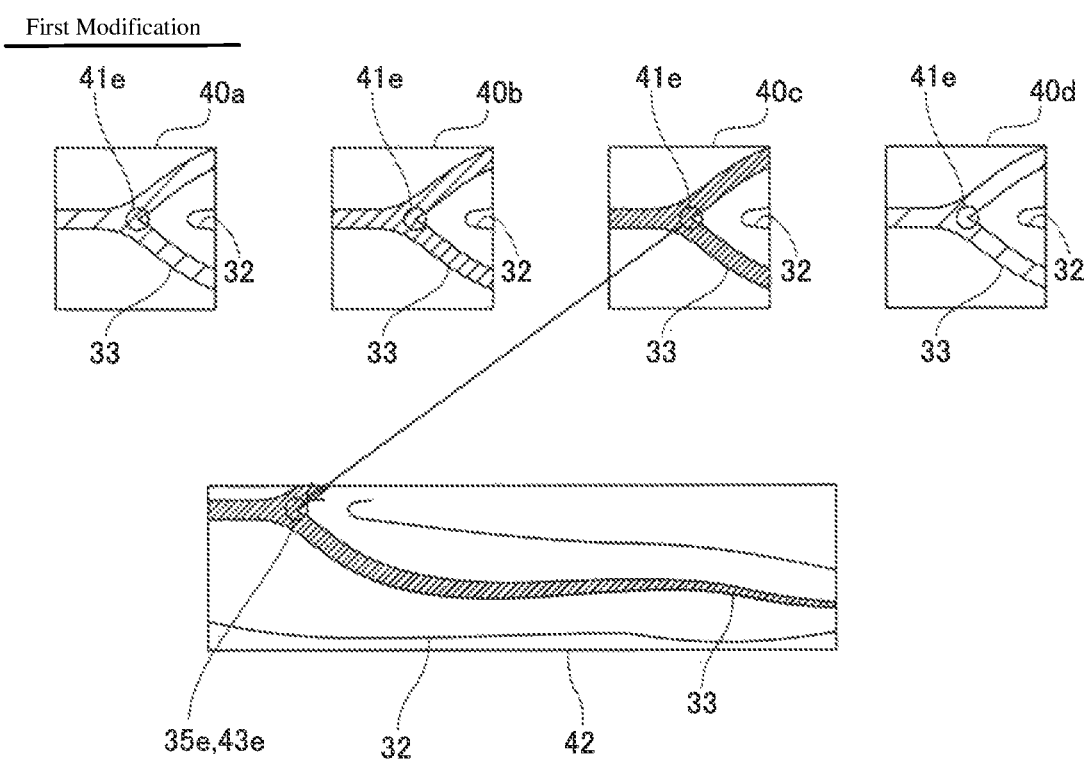
FIG. 13 is a schematic diagram for explaining the configuration for selecting a pixel value of a pixel corresponding point on a reference plane according to a first modification.

FIG. 13 is a schematic view showing an example in which the pixel 41e corresponding to the pixel corresponding point 35e (the pixel 43e of the subject image 42) on the reference plane 34 is reflected in the plurality of X-ray images (the X-ray image 40a, the X-ray image 40b, the X-ray image 40c, and the X-ray image 40d). The image processing unit 17 determines the pixel value of the pixel with the highest concentration of the contrast agent among the pixels 41e of the respective X-ray images as the pixel value of the pixel corresponding point. In the X-ray image, the image processing unit 17 normalizes the background portion in the X-ray image and performs the relative comparison of the pixel values of the contrast agent (the blood vessel 33) to select the pixel with the highest concentration of the contrast agent. In a case where the X-rays emitted from the X-ray source 9 do not change, the image processing unit 17 may be configured to select the pixel with a lower pixel value of the pixel of the X-ray image as the pixel with the highest concentration of the contrast agent. Note that in the example shown in FIG. 13, the difference in the concentration of the contrast agent is represented by the difference in the hatching intervals. Specifically, the smaller the hatching interval is, the higher the concentration of the contrast agent is.

According to the above-described configuration, in a case where there is a plurality of X-ray images in which the pixel corresponding points are reflected, the pixel value of the pixel with the highest concentration of the contrast agent is selected. Therefore, the image processing unit 17 can select the pixel value of the pixel in which the blood vessel 33 is most clearly reflected as the pixel value of the pixel corresponding point on the reference plane 34. As a result, the subject image 42 is generated based on the pixel value of the most clearly reflected pixel in the plurality of X-ray images (the X-ray image 40a, the X-ray image 40b, the X-ray image 40c, and the X-ray image 40d). Therefore, it is possible to generate the subject image 42 in which the blood vessel 33 is most clearly reflected.

(Second Modification)

In the above-described embodiment, an example is shown in which the image processing unit 17 is configured to generate the subject image 42 based on the plurality of X-ray images (the X-ray image 40a, the X-ray image 40b, the X-ray image 40c, and the X-ray image 40d) captured while moving the top board 1 only in the X-direction, but the present invention is not limited thereto. For example, as in the second modification shown in FIG. 14, the image processing unit 17 may be configured to generate an elongated image 420 as the subject image along the traveling route on the reference plane 34, based on a plurality of X-ray images (the X-ray image 400a, the X-ray image 400b, the X-ray image 400c, the X-ray image 400d, the X-ray image 400e, the X-ray image 400f, the X-ray image 400g, and the X-ray image 400h) (see FIG. 15) acquired while being moved manually along an arbitrary traveling route.

Figure 14:
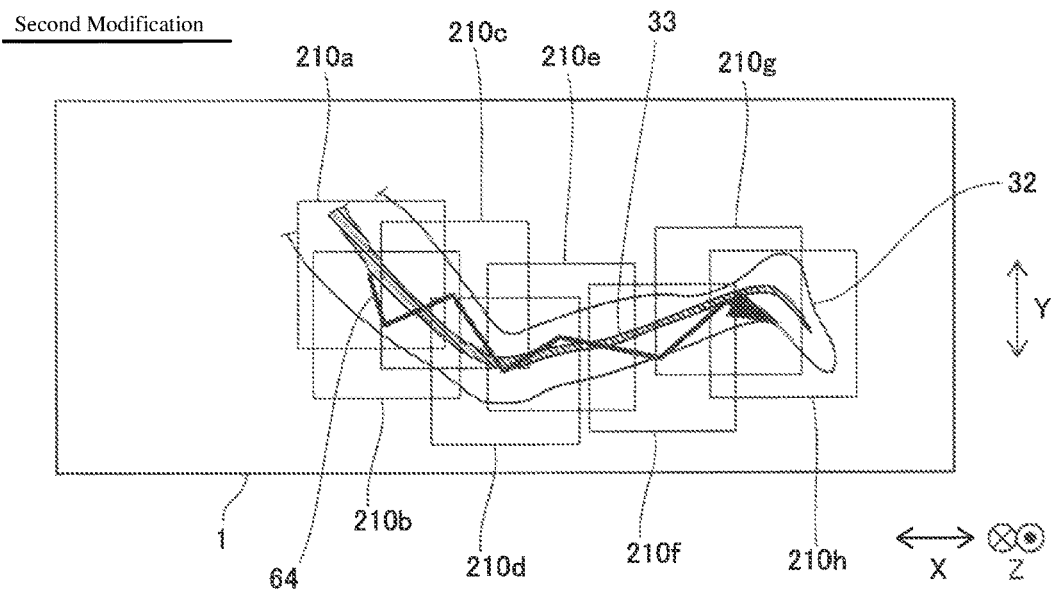
FIG. 14 is a schematic diagram for explaining a plurality of imaging positions along an arbitrary traveling route according to a second modification.

In the second modification, as shown in FIG. 14, imaging is performed while moving the top board 1 to a plurality of imaging positions along the arbitrary traveling route indicated by the arrow 64. Specifically, a plurality of X-ray images is captured while moving the top board 1 along the arrow 64 to the first imaging position 210a, the second imaging position 210b, the third imaging position 210c, the fourth imaging position 210d, the fifth imaging position 210e, the sixth imaging position 210f, the seventh imaging position 210g, and the eighth imaging position 210h. In addition to the configuration for performing the imaging while moving the top board 1 along an arbitrary traveling route, for example, a doctor or the like may perform the imaging while moving the imaging unit 2 along an arbitrary traveling route by gripping the holding portion (not shown) of the imaging unit 2 by hand. Further, imaging may be performed such that, for example, a doctor or the like operates the operation unit 8 to move the top board 1 or the imaging unit 2 along an arbitrary traveling route.

Figure 15:
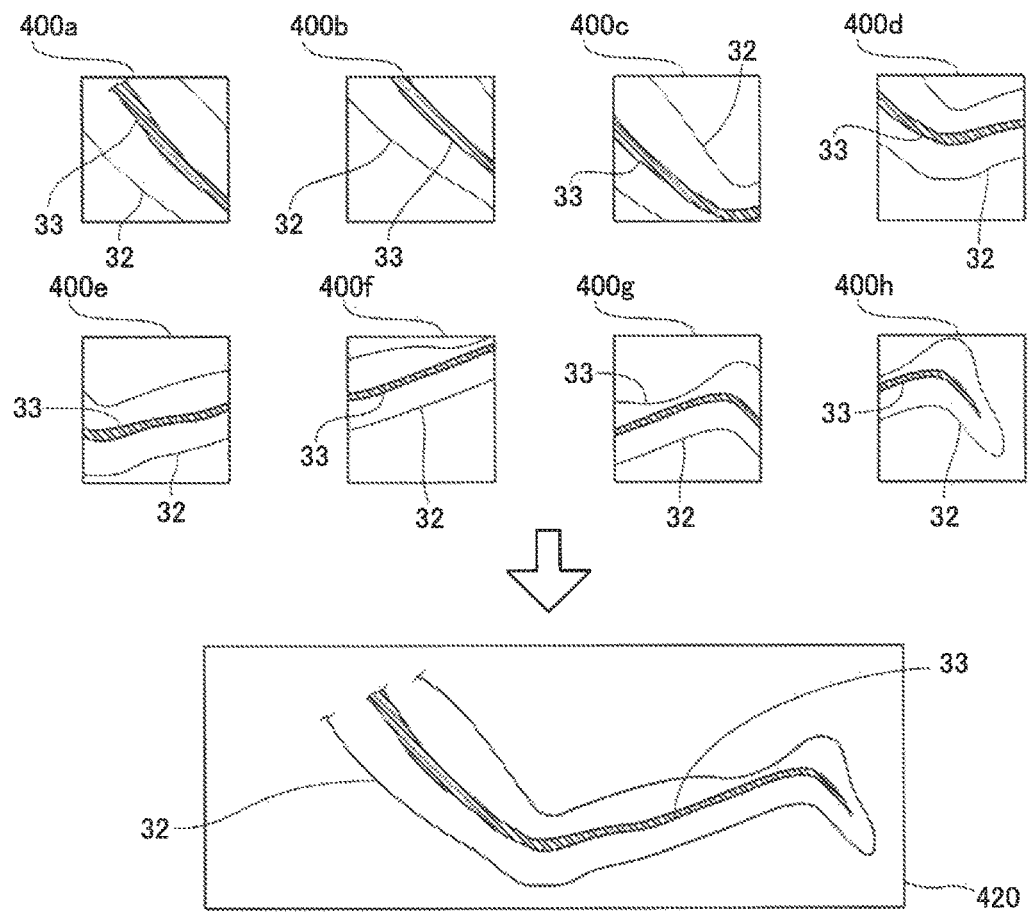
FIG. 15 is a schematic diagram for explaining the configuration for generating a subject image based on a plurality of images captured along an arbitrary traveling route according to the second modification.

As shown in FIG. 15, a plurality of X-ray images, i.e., the X-ray image 210a, the X-ray image 210b, the X-ray image 210c, the X-ray image 210d, X-ray image 210e, the X-ray image 210f, the X-ray image 210g, and the X-ray image 210h are captured at the respective imaging positions (the first imaging position 400b, the second imaging position 400c, the third imaging position 400d, the fourth imaging position 400e, the fifth imaging position 400f, the sixth imaging position 400g, the seventh imaging position 400h, and the eighth imaging position 400i). The image processing unit 17 generates an elongated image 420 as a subject image along the traveling route from the plurality of X-ray images in a manner similar to the above-described embodiment.

The image processing unit 17 selects the pixel value of each pixel corresponding point on the reference plane 34, based on a plurality of X-ray images (the X-ray image 400a, the X-ray image 400b, the X-ray image 400c, the X-ray image 400d, the X-ray image 400e, the X-ray image 400f, the X-ray image 400g, and the X-ray image 400h) to generate the elongated image 420 as the subject image. Note that the arbitrary traveling route is not limited to the direction indicated by the arrow 64 in FIG. 14. Since the moving mechanism 4 is configured to allow the top board 1 to be moved arbitrarily in any direction of the X-direction, the Y-direction, and the Z-direction, the traveling route may be an arbitrary traveling route along a traveling route in which the X-direction, the Y-direction, and the Z-direction are combined.

With the above-described configuration, even in a case where the top board 1 is moved along an arbitrary traveling route, the elongated image 420 as the subject image is generated. Therefore, the degree of freedom of selecting the traveling route can be improved. As a result, even in a case where a doctor or the like moves the imaging unit 2 in any direction while following the blood flow of the blood vessel 33 of the lower limb, the elongated image 420 as a subject image is generated. Therefore, the convenience of the user can be improved. In the case of a lower limb, in some cases, the lower limb cannot be extended depending on a patient. Even in such a case, the imaging along the bent lower limb can be performed without the need for pre-registration of the traveling route. Further, by generating the elongated image 420 projected on the reference plane 34 for the respective X-ray images (the X-ray image 400a, the X-ray image 400b, the X-ray image 400c, the X-ray image 400d, the X-ray image 400e, the X-ray image 400f, the X-ray image 400g, and the X-ray image 400h) captured along the arbitrary traveling route, the effect of parallax generated in an arbitrary direction can be effectively removed, thereby generating an image with higher visibility.

(Third Modification)

Further, in the above-described embodiment, an example is shown in which the image processing unit 17 is configured to generate the subject image 42, based on the plurality of X-ray images (the X-ray image 40a, the X-ray image 40b, the X-ray image 40c, and the X-ray image 40d) captured while moving the top board 1 in a state in which the angle of the C-shaped arm 12 is fixed, but the present invention is not limited thereto. For example, the image processing unit 17 may be configured to generate a single subject image 42 based on a plurality of X-ray images captured by rotating the C-shaped arm 12 while moving the top board 1 by the moving mechanism 4.

Figure 16:
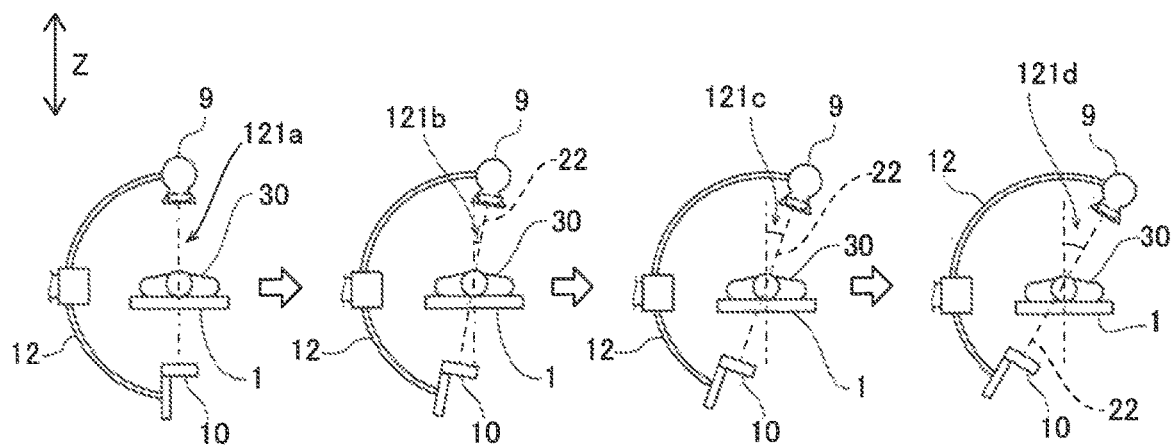
FIG. 16 is a schematic diagram for explaining the rotation of a C-shaped arm when capturing a plurality of images in an X-ray imaging apparatus according to a third modification.
Figure 17:
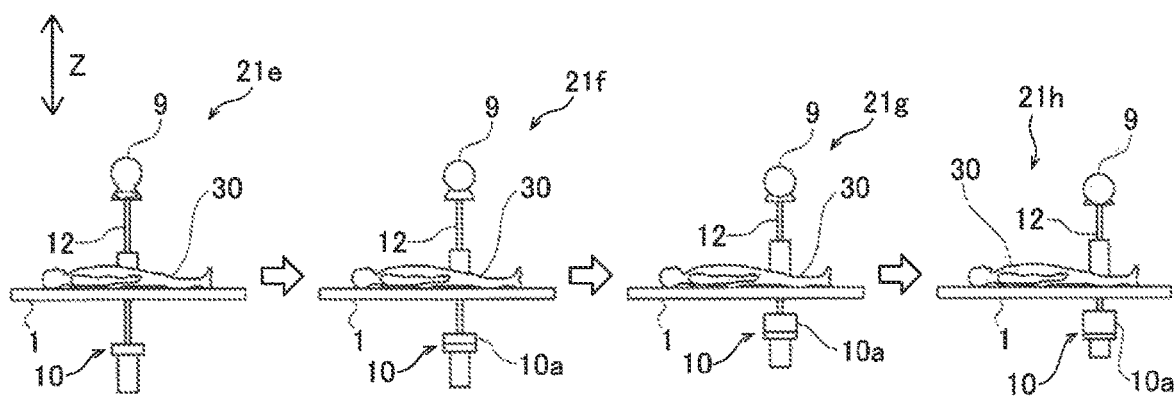
FIG. 17 is a schematic diagram for explaining the movement of a top board when capturing a plurality of images in the X-ray imaging apparatus according to the third modification.

FIG. 16 is a schematic diagram showing the C-shaped arm 12 at the time of the imaging when viewed from the X-direction in the X-ray imaging apparatus 100 according to a third modification. Further, FIG. 17 is a diagram showing the C-shaped arm 12 at the time of the imaging when viewed from the Y-direction in the X-ray imaging apparatus 100 according to the third modification.

As shown in FIG. 16, in the third modification, the X-ray imaging apparatus 100 captures a plurality of X-ray images while changing the rotation angle of the C-shaped arm 12. Further, as shown in FIG. 17, in the third modification, the X-ray imaging apparatus 100 captures a plurality of X-ray images while moving the top board 1. Specifically, as shown in FIGS. 16 and 17, a plurality of X-ray images are captured in a state in which the rotation angle of the C-shaped arm 12 is the first rotation angle 121a and the position of the top board 1 is the fifth imaging position 21e, a state in which the rotation angle of the C-shaped arm 12 is the second rotation angle 121b and the position of the top board 1 is the sixth imaging position 21f, a state in which the rotation angle of the C-shaped arm 12 is the third rotation angle 121c and the position of the top board 1 is the seventh imaging position 21g, and a state in which the rotation angle of the C-shaped arm 12 is the fourth rotation angle 121d and the position of the top board 1 is the eighth imaging position 21h.

That is, in the third modification, the X-ray imaging apparatus 100 is configured to capture a plurality of X-ray images while performing the rotation of the C-shaped arm 12 and the movement of the top board 1 simultaneously. Note that the rotation angle of the C-shaped arm 12 denotes the angle formed between the optical axis 22 of the X-rays and the Z-direction. The rotation angle of the C-shaped arm 12 is not limited to the above-described four angles. The rotation angle of the C-shaped arm 12 may be greater than or less than four. The position of the top board 1 is not limited to four. The position of the top board 1 may be more or less than four. The rotation angle of the C-shaped arm and the position of the top board 1 are arbitrarily set by a user.

With the above-described configuration, for example, even in a case where a plurality of blood vessels are present at positions overlapped in the Z-direction, the imaging can be performed by changing the angle of the C-shaped arm 12. Therefore, the plurality of blood vessels present at the positions overlapped in the Z-direction can be imaged from the oblique direction. As a result, the subject image 42 can be generated based on the plurality of X-ray images different in the imaging angle. Therefore, even in the case of imaging the blood vessels present at the positions overlapped in the Z-direction, it is possible to generate the subject image 42 capable of grasping the respective blood vessels.

(Fourth Modification)

Further, in the above-described embodiment, an example is shown in which the image processing unit 17 is configured to generate the subject image 42, based on a plurality of X-ray images (the X-ray image 40a, the X-ray image 40b, the X-ray image 40c, and the X-ray image 40d) captured while moving the top board 1 in a state of fixing the angle of the C-shaped arm, but the present invention is not limited thereto. For example, the image processing unit 17 may be configured to generate a plurality of subject images 42 at the respective angles, based on the X-ray images with the equal rotation angle of the C-shaped arm 12, among the plurality of X-ray images captured by rotating the C-shaped arm 12 while moving the top board 1 by the moving mechanism 4.

Figure 18:
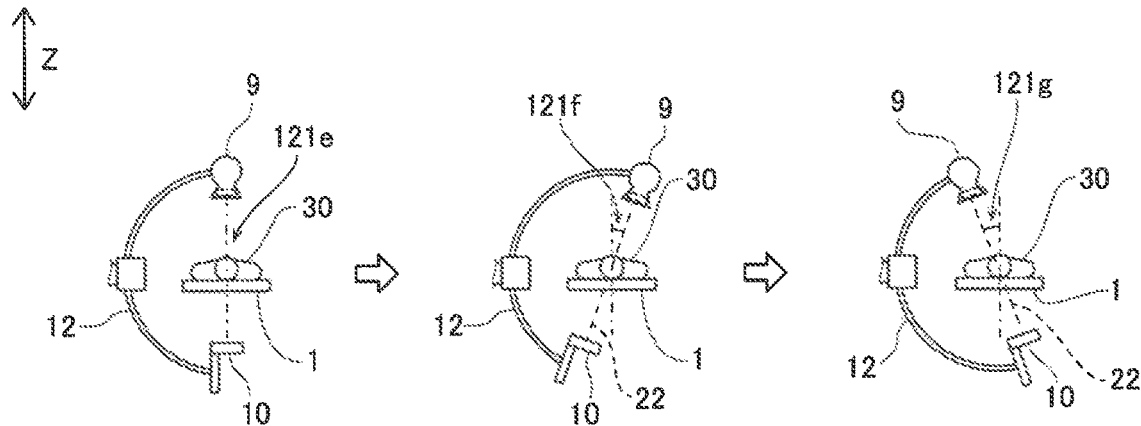
FIG. 18 is a schematic diagram for explaining the rotation of a C-shaped arm when capturing a plurality of images in an X-ray imaging apparatus according to a fourth modification.
Figure 18:

FIG. 18 is a schematic diagram showing the C-shaped arm 12 at the time of the imaging when viewed from the X-direction in the X-ray imaging apparatus 100 according to a fourth modification. Further, FIG. 19 is a schematic diagram showing the C-shaped arm 12 at the time of imaging when viewed from the Y-direction in the X-ray imaging apparatus 100 according to the fourth modification.

As shown in FIG. 18, in the third modification, the X-ray imaging apparatus 100 captures a plurality of X-ray images while changing the rotation angle of the C-shaped arm 12. In the example shown in FIG. 18, a plurality of X-ray images is captured while changing the rotation angle of the C-shaped arm 12 to the fifth rotation angle 121e, the sixth rotation angle 121f, and the seventh rotation angle 121g. Further, as shown in FIG. 19, in the fourth modification, the X-ray imaging apparatus 100 captures a plurality of X-ray images while moving the top board 1 to the fifth imaging position 21e to the eighth imaging position 21h.

Figure 19:
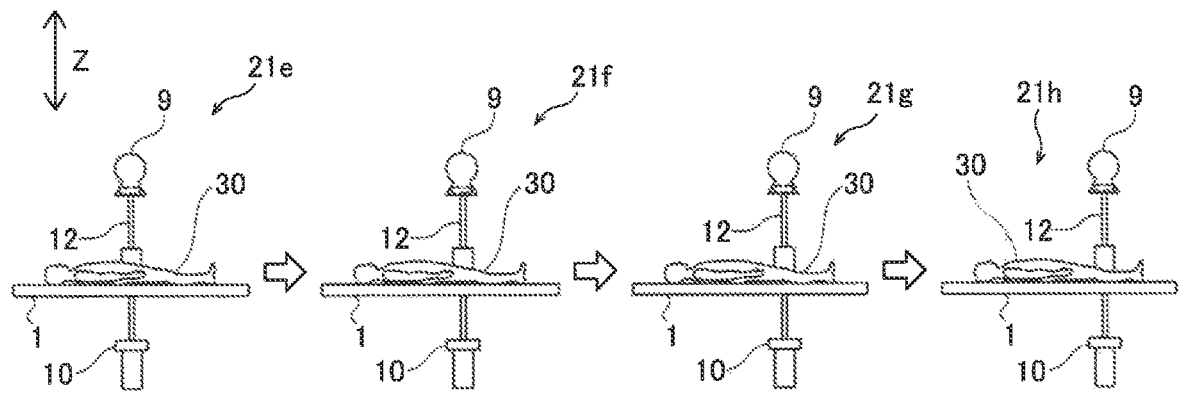
FIG. 19 is a schematic diagram for explaining the movement of the top board when capturing a plurality of images in the X-ray imaging apparatus according to the fourth modification.
Figure 19:
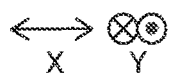

In the fourth modification, when moving the top board 1 as shown in FIG. 19, the X-ray images are captured at a plurality of rotation angles of the C-shaped arm 12 at the respective positions of the top board 1. More specifically, in a state in which the top board 1 is arranged at the fifth imaging position 21e, the imaging is performed by changing the rotation angle of the C-shaped arm 12 to the fifth rotation angle 121e, the sixth rotation angle 121f, and the seventh rotation angle 121g. Also in the sixth imaging position 21f, the seventh imaging position 21g, and the eighth imaging position 21h, similarly, in each imaging position, the imaging is performed by changing the rotation angle of the C-shaped arm 12 to the fifth rotation angle 121e to the seventh rotation angle 121g.

That is, the capturing X-ray images while rotating the C-shaped arm 12 and the movement of the top board 1 are alternately performed to thereby acquire the plurality pairs of X-ray images with the same rotation angle of the C-shaped arm 12 and different positions of the top board 1. The image processing unit 17 generates a plurality of subject images 42 based on a plurality of X-ray images with the same rotation angle of the C-shaped arm 12. In the example shown in FIG. 18, although the imaging is performed by arranging the C-shaped arm 12 at the three angles, the rotation angles of the C-shaped arm 12 are not limited to the angles shown in FIG. 18. The imaging may be performed while rotating the C-shaped arm 12 at three or more angles.

The position of the top board 1 is not limited to four positions. The top board 1 may be moved to more or less than four positions. The rotation angle of the C-shaped arm 12 and the position of the top board 1 are arbitrarily set by a user.

With the above-described configuration, the subject images 42 captured at a plurality of imaging angles can be generated based on the X-ray images captured at a plurality of imaging angles by a single administration of a contrast agent. As a result, in a case of performing the imaging at a plurality of imaging angles, the number of times of administering a contrast agent can be reduced, as compared with a configuration in which the imaging is performed by administering a contrast agent every time the imaging is performed at each imaging angle. This can reduce the burden on the subject 30. Further, it is possible to suppress the increase of the imaging time, as compared with the configuration in which the imaging at a plurality of imaging angles is performed for each angle.

(Fifth Modification)

Further, in the above-described embodiment, an example is shown in which the image processing unit 17 selects the pixel value of the pixel at a position close to the center of the X-ray image when selecting as the pixel value of the pixel corresponding point on the reference plane 34, the present invention is not limited thereto. For example, in a plurality of X-ray images (the X-ray image 40a, the X-ray image 40b, and the X-ray image 40c) (see FIG. 20), in a case where the distance from the center position of the X-ray image from the pixel (the pixel 41a, the pixel 41b, and the pixel 41c) (see FIG. 20) corresponding to the pixel corresponding point 35a (see FIG. 21) on the reference plane 34 is equal to each other, it may be configured to select the pixel value of the pixel corresponding point on the reference plane 34, based on the distance in the three-dimensional coordinate system between the reference plane 34 and the pixel in each X-ray image.

Figure 20:
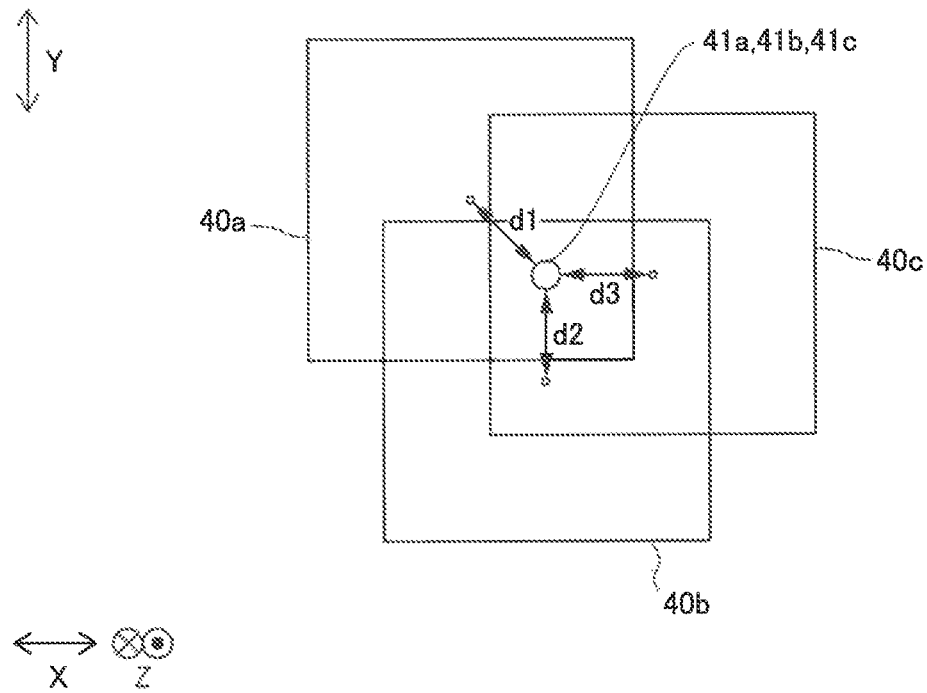
FIG. 20 is a schematic diagram for explaining a distance from the center of each image to a pixel corresponding point on a reference plane according to a fifth modification.

FIG. 20 is a schematic view for explaining the distance (the distance d1, the distance d2, the distance d3) between the pixel (the pixel 41a, the pixel 41b, and the pixel 41c) corresponding to the pixel corresponding point 35a (see FIG. 21) on the reference plane 34 and the center of each X-ray image, in a plurality of X-ray images (the X-ray image 40a, the X-ray image 40b, and the X-ray image 40c). In the X-ray image 40a, the X-ray image 40b, and the X-ray image 40c, the positions in which the pixels corresponding to the pixel corresponding points 35a on the reference plane 34 are reflected are different from each other. However, in each X-ray image, the distance (the distance d1, the distance d2, and the distance d3) between the pixel corresponding to the pixel corresponding point 35a on the reference plane 34 and the center of the image is equal to each other. In the fifth modification, in such a case, the image processing unit 17 is configured to select the pixel value of the pixel corresponding point 35a on the reference plane 34, based on each pixel (the pixel 41a, the pixel 41b, and the pixel 41c) and the three-dimensional distance from the reference plane 34.

Figure 21:
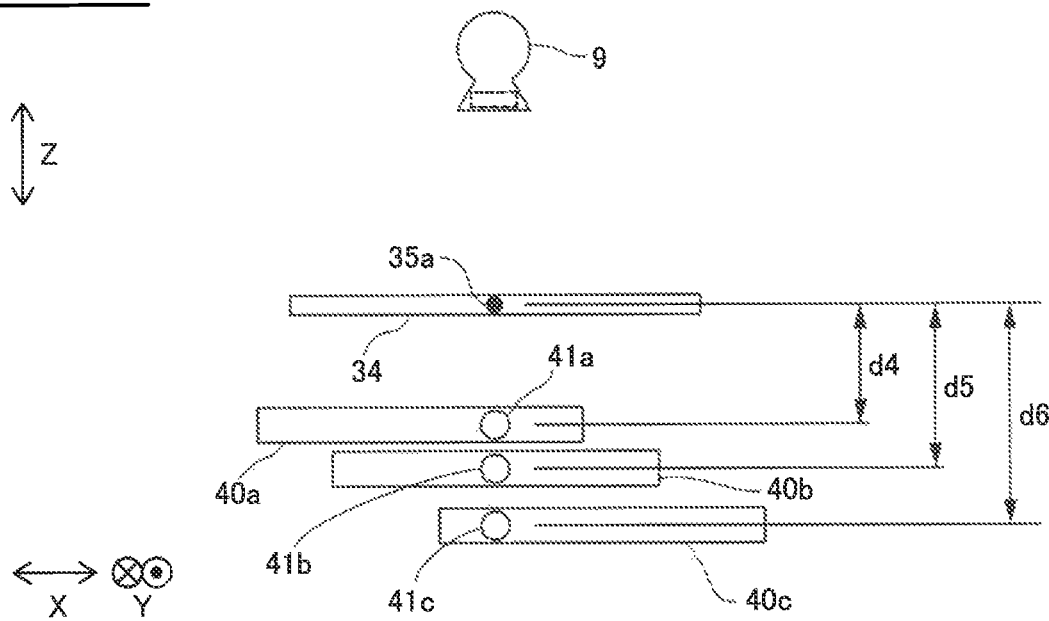
FIG. 21 is a schematic diagram for explaining the configuration for selecting an image including a pixel corresponding to the pixel corresponding point on the reference plane according to the fifth modification.

Here, in a case where the top board 1 is moved in a state in which the reference plane 34 is inclined with respect to the top board 1, the Z-directional position of the same pixel corresponding point 35a on the reference plane 34 changes. When the Z-directional position of the pixel corresponding point 35a changes, the magnification ratio changes. In other words, it can be considered that the distances between the respective X-ray images (the X-ray image 40a, the X-ray image 40b, and the X-ray image 40c) in which the pixel corresponding to the pixel corresponding point 35a on the reference plane 34 is reflected and the reference plane 34 are different. That is, as shown in FIG. 21, it can be regarded such that a plurality of X-ray images in which the pixel corresponding points 35a are reflected is positioned at different positions in the Z-direction. FIG. 21 is a schematic diagram showing the distances between each of the X-ray image 40a, the X-ray image 40b, and the X-ray image 40c and the reference plane 34. In the example shown in FIG. 21, the distance d4 is the smallest among the distance d4 between the X-ray image 40a and the reference plane 34, the distance d5 between the X-ray image 40b and the reference plane 34, and the distance d6 between the X-ray image 40c and the reference plane 34. Therefore, the image processing unit 17 selects the pixel value of the pixel 41a of the X-ray image 40a as the pixel value of the pixel corresponding point 35a on the reference plane 34.

With the above-described configuration, the pixel value of the pixel 41a at the position three-dimensionally closest to the reference plane 34 can be selected as the pixel value of the pixel corresponding point 35a on the reference plane 34. As a result, the effect of distortion of the image due to the X-ray radiation angle can be reduced, which can suppress the resulting subject image 42 from becoming an unnatural image. Further, even in a case where there is a plurality of pixels with the same distance from the center of the X-ray image, it is possible to easily determine the pixel 41a in which the pixel corresponding point 35a is most clearly reflected.

(Sixth Modification)

Figure 22:
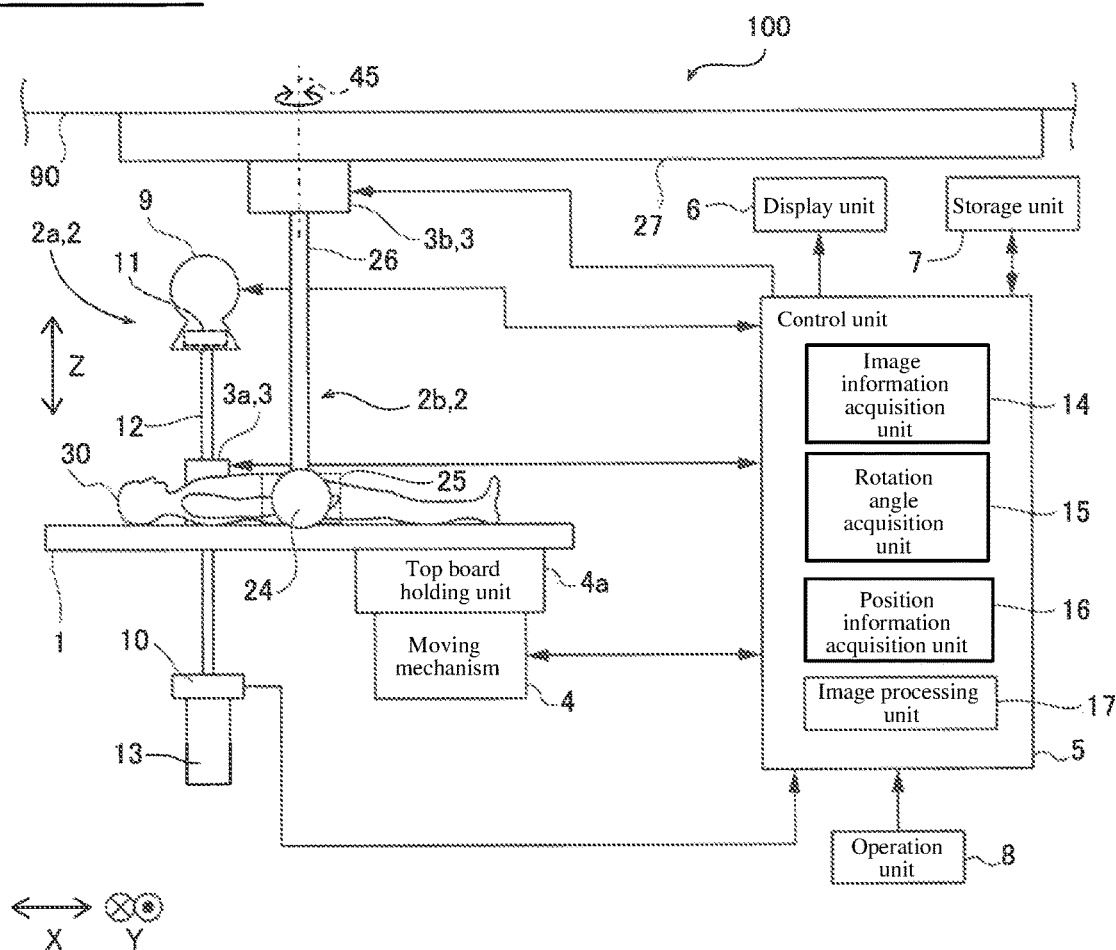
FIG. 22 is a schematic diagram showing the entire configuration of an X-ray imaging apparatus according to a sixth modification.

Further, in the above-described embodiment, an example is shown in which the subject 30 is imaged by a single imaging unit 2, but the present invention is not limited thereto. For example, as shown in FIG. 22, the imaging unit 2 may include a first imaging unit 2a and a second imaging unit 2b. The second imaging unit 2b is configured to capture a plurality of X-ray images (the X-ray image 40a, the X-ray image 40b, the X-ray image 40c, and the X-ray image 40d) while being inclined at an angle different from that of the first imaging unit 2a with respect to the subject 30. Note that in the drawings, the same components as those of the above-described embodiments are allocated by the same reference symbols.

As shown in FIG. 22, the X-ray imaging apparatus 100 according to the sixth modification may be configured as a so-called bi-plane X-ray imaging apparatus in which the imaging unit 2 includes a first imaging unit 2a and a second imaging unit 2b, the second imaging unit 2b being configured to image a plurality of X-ray images in a state of being inclined at an angle different from that of the first imaging unit 2a with respect to the subject 30. The first imaging unit 2a is arranged at a position sandwiching the top board 1 in the Z-direction. Further, the second imaging unit 2b is arranged at a position sandwiching the top board 1 in the Y-direction. Further, in the X-ray imaging apparatus 100 according to the sixth modification, the rotation mechanism 3 includes a first rotation mechanism 3a capable of rotating the first imaging unit 2a and a second rotation mechanism 3b capable of rotating the second imaging unit 2b.

The first imaging unit 2a includes an X-ray source 9 and an X-ray detection unit 10. Further, the second imaging unit 2b includes an X-ray source 24 and an X-ray detection unit 25. The X-ray source 24 includes a collimator 28. The X-ray source 24, the X-ray detection unit 25, and the collimator 28 have the same configuration as the X-ray source 9, the X-ray detection unit 10, and the collimator 11 in the first embodiment, and therefore, the detailed description thereof will be omitted.

Since the first rotation mechanism 3a has the same configuration as that of the rotation mechanism 3 in the above-described embodiment, the detailed descriptions thereof will be omitted.

The second rotation mechanism 3b holds the second imaging unit 2b via the C-shaped arm 26. The second rotation mechanism 3b is configured to be capable of rotating the second imaging unit 2b by rotating the C-shaped arm 26. The second rotation mechanism 3b includes the moving mechanism for moving the C-shaped arm 26 along the outer periphery of the C-shaped arm 26. Further, the second rotation mechanism 3b is held by the moving mechanism 27 mounted on the ceiling 90. The moving mechanism 27 is configured to be capable of moving the second rotation mechanism 3 b in the X-direction. Further, the moving mechanism 27 is configured to be capable of rotating the second rotation mechanism 3b about the axis of the straight line 45.

Figure 23:
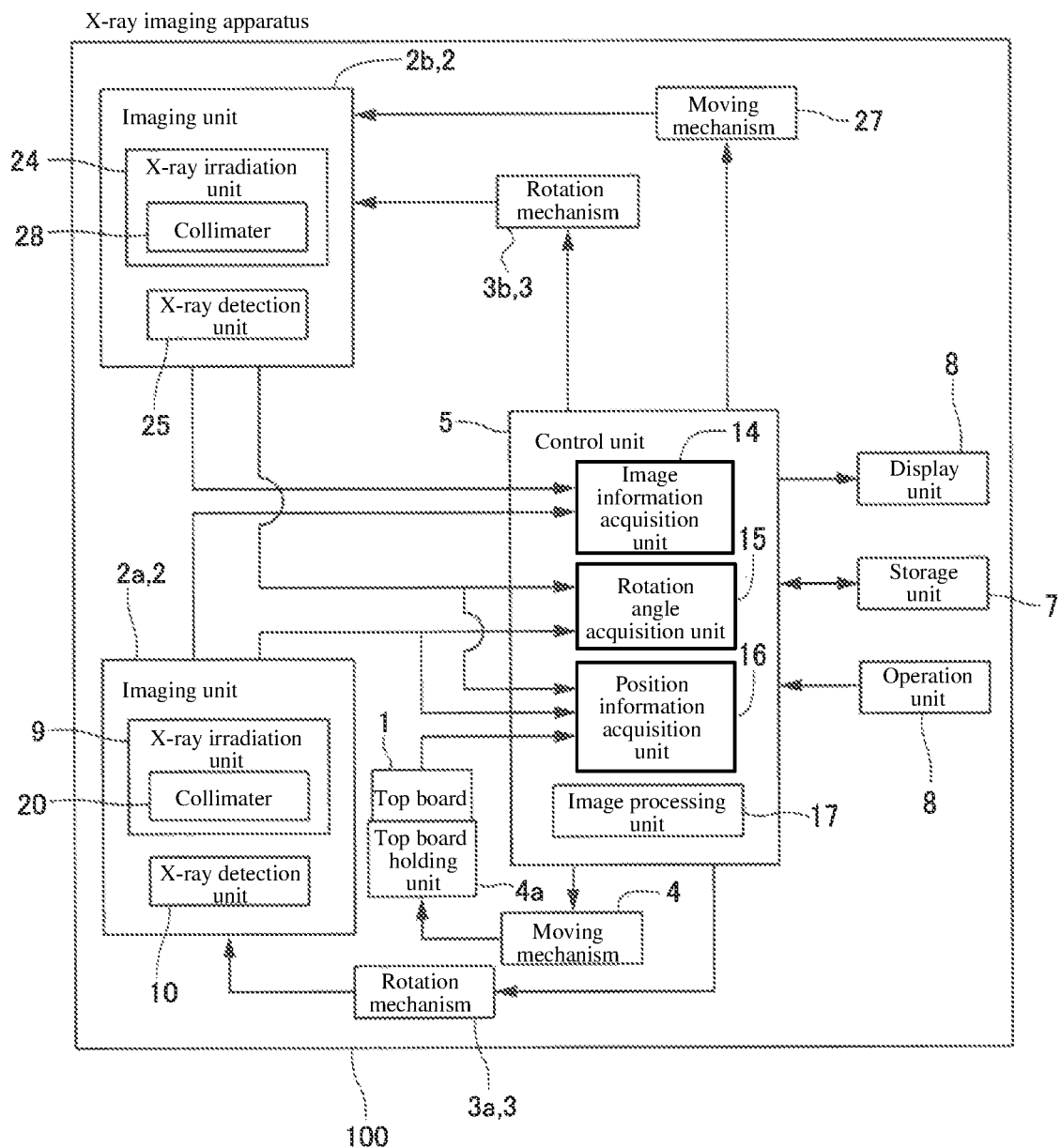
FIG. 23 is a block diagram showing the entire configuration of the X-ray imaging apparatus according to the sixth modification.

As shown in FIG. 23, the image information acquisition unit 14 according to the sixth modification is configured to acquire the image information captured by the first imaging unit 2a from the X-ray detection unit 10. Further, the image information acquisition unit 14 according to the sixth modification is configured to acquire the image information captured by the second imaging unit 2b from the X-ray detection unit 25. Further, in the sixth modification, the rotation angle acquisition unit 15 is configured to acquire the rotation angle of the first imaging unit 2a and the rotation angle of the second imaging unit 2b acquired by the first imaging unit 2a and the second imaging unit 2b, respectively.

In the sixth modification, the image processing unit 17 is configured to generate an X-ray image captured by the first imaging unit 2a and the X-ray image captured by the second imaging unit 2b, based on the image information acquired by the image information acquisition unit 14. Further, in the sixth modification, the image processing unit 17 is configured to generate the subject image 42, based on the plurality of X-ray images captured by the first imaging unit 2a. Further, the image processing unit 17 is configured to generate the subject image 42 based on the plurality of X-ray images captured by the second imaging unit 2b. The configuration in which the image processing unit 17 generates the subject image 42 is the same as that of the above-described embodiments, and therefore the detailed explanation thereof will be omitted.

Figure 24:
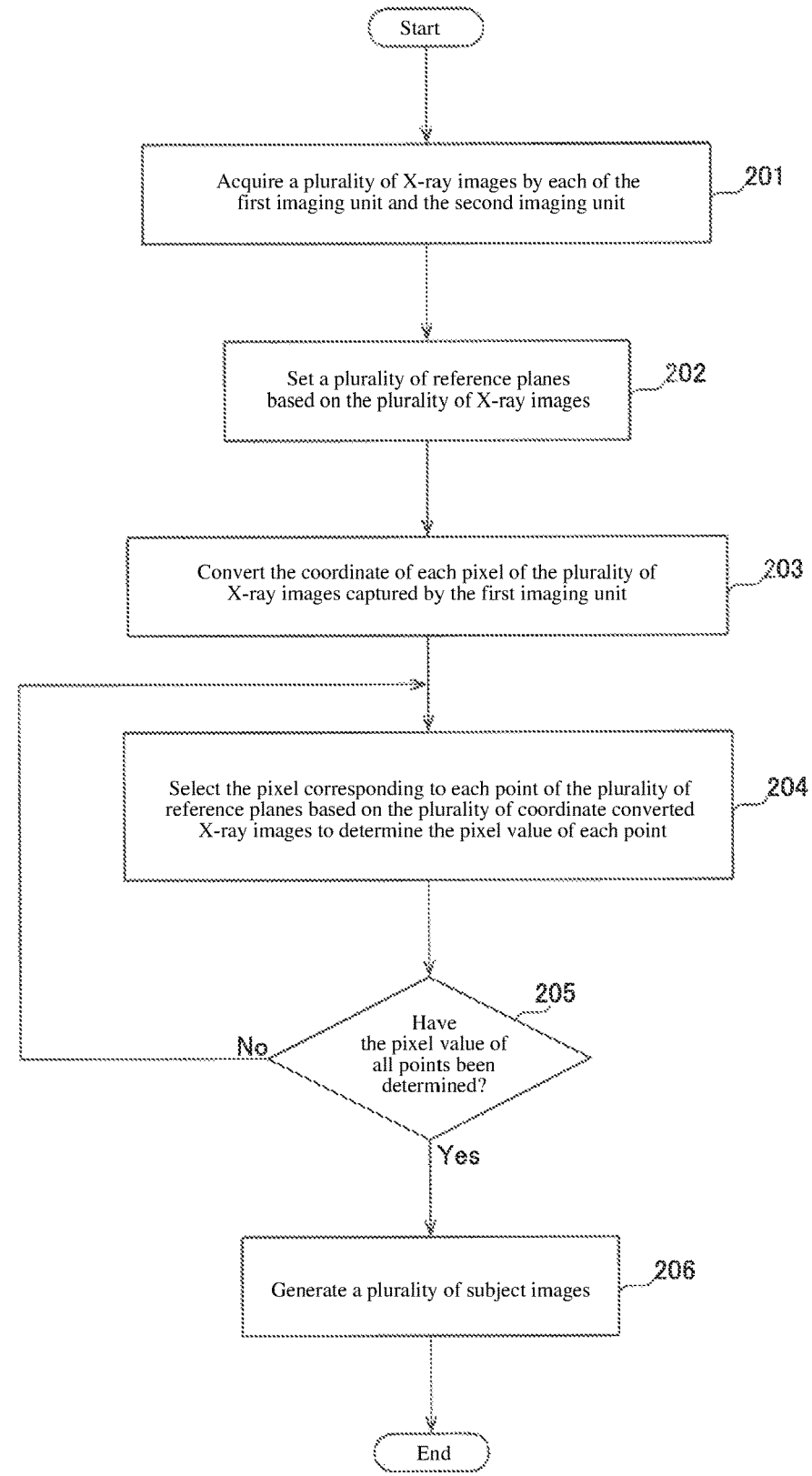
FIG. 24 is a flowchart for explaining the generation processing of a subject image in the X-ray imaging apparatus according to the sixth modification.

Next, referring to FIG. 24, the processing in which the X-ray imaging apparatus 100 in the sixth modification generates the subject image 42 will be described.

In Step 201, the image processing unit 17 acquires a plurality of X-ray images captured by the first imaging unit 2a and the second imaging unit 2b.

Next, in Step 202, the image processing unit 17 sets a plurality of reference planes 34 based on a plurality of X-ray images captured by the first imaging unit 2a and a plurality of X-ray images captured by the second imaging unit 2b.

Next, in Step 203, the image processing unit 17 performs the coordinate transformation of the respective pixels with respect to the plurality of X-ray images captured by the first imaging unit 2a and the second imaging unit 2b.

Next, in Step 204, the image processing unit 17 selects the pixel corresponding to each pixel corresponding point on each reference plane 34 based on a plurality of X-ray images captured by the first imaging unit 2a and the second imaging unit 2b after the coordinate transformation has been performed and determines the pixel value of each pixel corresponding point.

Next, in Step 205, the image processing unit 17 determines whether or not the pixel values of all pixel corresponding points on the respective reference planes 34 have been determined. When the pixel values of all pixel corresponding points on the respective reference plane 34 have been determined, the processing proceeds to Step 206. When the pixel values of all pixel corresponding points on the respective reference planes 34 have not been determined, the processing proceeds to Step 204.

In Step 206, the image processing unit 17 generates the subject image 42 on the respective reference planes 34. Thereafter, the processing ends.

With the above-described configuration, the subject images 42 captured at angles different from each other can be acquired by the first imaging unit 2a and the second imaging unit 2b by administering a contrast agent once. As a result, as compared with the configuration in which imaging is performed by changing the imaging angle by administering a contrast agent a plurality of times by a single imaging unit 2, it is possible to suppress an increase in the number of times of administering a contrast agent. Further, the exposure dose can be reduced because the imaging time can be shortened.

(Other Modifications)

In addition, in the above-described embodiments, an example is shown in which in a case where there is a plurality of X-ray images in which the pixel corresponding points are reflected, the image processing unit 17 is configured to select the pixel value of the pixel at the position closest to the center of the X-ray image as the pixel in which the pixel corresponding point is most clearly reflected, but the present invention is not limited thereto. For example, in a case where there is a plurality of X-ray images in which the pixel corresponding points are reflected, the image processing unit 17 may be configured to determine the pixel value of the pixel corresponding point by selecting the pixel value of the pixel with the lowest pixel value among the pixels corresponding to the pixel corresponding points as the pixel in which the pixel corresponding point is most clearly reflected among the pixels corresponding to the pixel corresponding points in the plurality of X-ray images. With this configuration, the pixel value of the pixel with the lowest pixel value is selected as the pixel value of the pixel corresponding point. Therefore, it is possible to generate the subject image 42 with the high contrast of the portion of the subject 30 to be observed. Consequently, it is possible to easily grasp the portion to be observed in the subject image 42

In the above-described embodiment, an example is shown in which the reference plane 34 is a plane along the detection surface 10a of the X-ray detection unit 10, but the present invention is not limited thereto. For example, the reference plane 34 may be a plane along the top board 1. However, in a case where the reference plane 34 is a plane along the top board 1, it is preferable that the reference plane 34 is a plane along the detection surface 10a of the X-ray detection unit 10 because the reference plane 34 becomes a plane different from a plane intended by a doctor or the like when imaging is performed in a state in which the imaging unit 2 is inclined with respect to the top board 1.

Further, in the above-described embodiment, an example is shown in which the reference plane 34 is a flat plane, but the present invention is not limited thereto. For example, the reference plane 34 may be a curved plane. However, in a case where the reference plane 34 is a curved plane, the magnification ratio differs between the center of the subject image 42 and the end of the subject image 42, resulting in an unnatural image of the subject image 42. Therefore, the reference plane 34 is preferable a flat plane.

In the above-described embodiment, an example is shown in which the moving mechanism 4 is provided with the top board holding unit 4a, but the present invention is not limited thereto. In a case where the moving mechanism 4 moves the top board 1 automatically, the top board holding unit 4a is not always required to be provided. However, in a case where the top board 1 is moved while changing the moving speed thereof, for example, in such a case that the imaging is performed while following a blood flow of a blood vessel, it is preferred to move the top board 1 manually. Therefore, the moving mechanism 4 is preferably provided with the top board holding unit 4a.

Further, in the above-described embodiment, an example is shown in which the moving mechanism 4 is provided with the C-shaped arm 12, but the present invention is not limited thereto. For example, the moving mechanism 4 may not be provided with the C-shaped arm 12. In a case where the moving mechanism 4 is not provided with the C-shaped arm 12, the X-ray source 9 and the X-ray detection unit 10 may be mounted on the ceiling and the floor, respectively. However, in a case where the moving mechanism 4 is not provided with the C-shaped arm 12, it is necessary to adjust the angle of the X-ray source 9 and that of the X-ray detection unit 10 when imaging in a state in which the imaging unit 2 is inclined with respect to the top board 1. Thus, it becomes complicated to change the angle of the imaging unit 2. For this reason, the moving mechanism 4 is preferably provided with the C-shaped arm 12.

Further, in the above-described embodiment, an example is shown in which the image processing unit 17 converts the coordinate on a pixel-by-pixel basis when performing the coordinate transformation of the plurality of X-ray images (the X-ray image 40a, the X-ray image 40b, the X-ray image 40c, and the X-ray image 40d), but the present invention is not limited thereto. For example, the image processing unit 17 may be configured to perform the coordinate transformation on an image-by-image basis, representing the coordinate of the pixel at the center of a plurality of X-ray images. With this configuration, the processing rate of the coordinate transformation can be improved, as compared with the configuration in which the coordinate transformation is performed on a pixel-by-pixel basis. However, when the coordinate transformation is performed at the edge of the image, the accuracy of the coordinate transformation is lowered, as compared with the configuration in which the coordinate transformation is performed on a pixel-by-pixel basis. Therefore, the image processing unit 17 is preferably configured to perform the coordinate transformation on a pixel-by-pixel basis.

Further, in the above-described embodiment, for convenience of explanation, an example is shown in which the control processing of the control unit 5 has been described using a flow-driven flowchart in which processing is performed in order along the processing flow, but the present invention is not limited thereto. In the present invention, the control processing of the control unit 5 may be performed by an event-driven processing that executes processing on an event-by-event basis. In this case, the processing of the control unit may be performed in a complete event-driven fashion or in combination of the event-driven processing and the flow-driven processing.

It will be appreciated by those skilled in the art that the above-described exemplary embodiments are illustrative of the following aspects.

(Item 1)

An X-ray imaging apparatus comprising:

an imaging unit including an X-ray source for irradiating a subject with X-rays and an X-ray detection unit for detecting the X-rays transmitted through the subject, the imaging unit being configured to capture an image;

a moving mechanism including a top board for placing the subject thereon, the moving mechanism being capable of moving at least one of the top board and the imaging unit to change a relative position between the top board and the imaging unit;

an image processing unit configured to acquire a plurality of images while changing the relative position by the moving mechanism and generate a subject image based on the plurality of images, wherein the image processing unit is configured to set a reference plane that is an imaging region when generating the subject image based on the plurality of images and determine pixel values of a plurality of pixel corresponding points included in the reference plane based on the plurality of images to generate the subject image on the reference plane, and wherein in a case where there is a plurality of images in which the pixel corresponding points are reflected, the image processing unit is configured to select a pixel corresponding to the pixel corresponding point in the image in which the pixel corresponding point is most clearly reflected among the plurality of images to determine the pixel value of the pixel corresponding point.

(Item 2)

The X-ray imaging apparatus as recited in the above-described Item 1, wherein in a case where there is a plurality of images in which the pixel corresponding points are reflected, the image processing unit is configured to select a pixel value of a pixel at a position closest to a center of the image as a pixel in which the pixel corresponding point is most clearly reflected among pixels corresponding to the pixel corresponding points on the reference plane in the plurality of images to determine the pixel value of the pixel corresponding point.

(Item 3)

The X-ray imaging apparatus as recited in the above-described Item 1, wherein at least one of the plurality of images is an image in which a contrast agent administered to the subject is reflected, and wherein in a case where there is a plurality of images in which the pixel corresponding points are reflected, the image processing unit is configured to select a pixel value of a pixel with the highest concentration of the contrast agent as a pixel in which the pixel corresponding point is most clearly reflected among pixels corresponding to the pixel corresponding points in the plurality of images to determine a pixel value of the pixel corresponding point.

(Item 4)

The X-ray imaging apparatus as recited in the above-described Item 1, wherein in a case where there is a plurality of images in which the pixel corresponding points are reflected, the image processing unit is configured to select a pixel value of a pixel with the lowest pixel value among pixels corresponding the pixel corresponding points in the plurality of images as a pixel in which the pixel corresponding point is most clearly reflected among pixels corresponding to the pixel corresponding points in the plurality of images to determine a pixel value of the pixel corresponding point.

(Item 5)

The X-ray imaging apparatus as recited in the above-described Item 1, wherein the reference plane is a plane along a detection surface of the X-ray detection unit.

(Item 6)

The X-ray imaging apparatus as recited in the above-described Item 1, wherein the reference plane is a flat plane.

(Item 7)

The X-ray imaging apparatus as recited in the above-described Item 1, wherein the reference plane is a plane in which a magnification ratio of each of the plurality of the images is constant.

(Item 8)

The X-ray imaging apparatus as recited in the above-described Item 1, wherein the moving mechanism further includes a top board holding unit for holding the top board at least in a plane in a manually movable manner.

(Item 9)

The X-ray imaging apparatus as recited in the above-described Item 8, wherein the image processing unit is configured to generate, based on a plurality of images acquired while being moved manually along an arbitrary traveling route, an elongated image as the subject image along the traveling route on the reference plane.

(Item 10)

The X-ray imaging apparatus as recited in the above-described Item 8, wherein the moving mechanism further includes a C-shaped arm for integrally holding the X-ray source and the X-ray detection unit.

(Item 11)

The X-ray imaging apparatus as recited in the above-described Item 10, wherein the image processing unit is configured to generate a single subject image based on a plurality of images captured by rotating the C-shaped arm while moving the top board by the moving mechanism.

(Item 12)

The X-ray imaging apparatus as recited in the above-described Item 10, wherein the image processing unit is configured to generate the plurality of subject images at respective angles based on the images with the same rotation angle of the C-shaped arm among the plurality of images captured by rotating the C-shaped arm while moving the top board by the moving mechanism.

DESCRIPTION OF SYMBOLS

1: Top board
2, 2a, 2b: Imaging unit
4: Moving mechanism
4a: Top board holding unit
9, 24: X-ray source;
10, 25: X-ray detection unit
10a: Detection surface
12: C-shaped arm
17: Image processing unit
30: Subject
34: Reference plane
35a, 35b, 35c, 35d, 35e: Pixel corresponding point
40a, 40b, 40c, 40d, 400a, 400b, 400c, 400d, 400e, 400f, 400g, 400h: X-ray Image
41a, 41b, 41c, 41d, 41e; Pixel corresponding to pixel corresponding point
42: Subject image
100: X-ray imaging apparatus
420: Elongated image

The invention claimed is:

1. An X-ray imaging apparatus comprising:

an imaging unit including an X-ray source for irradiating a subject with X-rays and an X-ray detection unit for detecting the X-rays transmitted through the subject, the imaging unit being configured to capture an original image which includes a plurality of pixels;

a moving mechanism including a top board for placing the subject thereon, the moving mechanism being capable of moving at least one of the top board and the imaging unit to change a relative position between the top board and the imaging unit; and an image processing unit configured to acquire a plurality of original images while changing the relative position by the moving mechanism and generate a subject image based on the plurality of original images, set a reference plane that includes a plurality of pixel corresponding points and is an imaging region of the subject image based on the plurality of original images and determine pixel values of the plurality of pixel corresponding points included in the reference plane based on the plurality of original images coordinate-transformed on the reference plane to generate the subject image on the reference plane, identify the original image captured with an incident of the X-ray irradiated from the X-ray source to the pixel corresponding point for each of the plurality of pixel corresponding points, in a case where the original image which is identified is a single image, determine the pixel value of a reached pixel of the X-ray irradiated from the X-ray source and passed through the pixel corresponding point among the plurality of pixels in the identified original image as the pixel value of the pixel corresponding point, and in a case where there is a plurality of original images which is identified, determine the pixel value of a reached pixel of the X-ray irradiated from the X-ray source and passed through the pixel corresponding point in the identified original image in which the difference value between the pixel value of the reached pixel and a pixel value of a background portion is large, among the plurality of original images, as the pixel value of the pixel corresponding point.

2. The X-ray imaging apparatus as recited in claim 1, wherein at least one of the plurality of original images is an original image in which a contrast agent administered to the subject is reflected, and wherein in a case where there is a plurality of original images in which is identified, the image processing unit is configured to select a pixel value of a pixel with the highest concentration of the contrast agent as a pixel in which the pixel corresponding point is most clearly reflected among pixels corresponding to the pixel corresponding points in the plurality of original images to determine a pixel value of the pixel corresponding point.

3. The X-ray imaging apparatus as recited in claim 1, wherein in a case where there is a plurality of original images in-which is identified, the image processing unit is configured to select a pixel value of a pixel with the lowest pixel value among pixels corresponding to the pixel corresponding points in the plurality of original images as a pixel in which the pixel corresponding point is most clearly reflected among pixels corresponding to the pixel corresponding points in the plurality of original images to determine a pixel value of the pixel corresponding point.

4. The X-ray imaging apparatus as recited in claim 1, wherein the reference plane is a plane along a detection surface of the X-ray detection unit.

5. The X-ray imaging apparatus as recited in claim 1, wherein the reference plane is a flat plane.

6. The X-ray imaging apparatus as recited in claim 1, wherein the reference plane is a plane in which a magnification ratio of each of the plurality of the original images is constant.

7. The X-ray imaging apparatus as recited in claim 1, wherein the moving mechanism further includes a top board holding unit for holding the top board at least in a plane in a manually movable manner.

8. The X-ray imaging apparatus as recited in claim 7, wherein the image processing unit is configured to generate, based on a plurality of original images acquired while the top board is being moved manually along an arbitrary traveling route, an elongated image as the subject image along the traveling route on the reference plane.

9. The X-ray imaging apparatus as recited in claim 7, wherein the moving mechanism further includes a C-shaped arm for integrally holding the X-ray source and the X-ray detection unit.

10. The X-ray imaging apparatus as recited in claim 9, wherein the image processing unit is configured to generate a single subject image based on a plurality of original images captured by rotating the C-shaped arm while moving the top board by the moving mechanism.

11. The X-ray imaging apparatus as recited in claim 10, wherein the image processing unit is configured to generate a plurality of subject images at respective angles based on the images with a same rotation angle of the C-shaped arm among the plurality of original images captured by rotating the C-shaped arm while moving the top board by the moving mechanism.

12. An X-ray imaging apparatus comprising:
an imaging unit including an X-ray source for irradiating a subject with X-rays and an X-ray detection unit for detecting the X-rays transmitted through the subject, the imaging unit being configured to capture an image;
a moving mechanism including a top board for placing the subject thereon, the moving mechanism being capable of moving at least one of the top board and the imaging unit to change a relative position between the top board and the imaging unit; and
an image processing unit configured to acquire a plurality of images while changing the relative position by the moving mechanism and generate a subject image based on the plurality of images,
wherein the image processing unit is configured to set a reference plane that is an imaging region when generating the subject image based on the plurality of images and determine pixel values of a plurality of pixel corresponding points included in the reference plane based on the plurality of images coordinate-transformed on the reference plane to generate the subject image on the reference plane,
wherein in a case where there is a plurality of images in which the pixel corresponding points are reflected, the image processing unit is configured to select a pixel corresponding to the pixel corresponding point in the image in which the pixel corresponding point is most clearly reflected among the plurality of images to determine the pixel value of the pixel corresponding point, and
wherein in a case where there is a plurality of images in which the pixel corresponding points are reflected, the image processing unit is configured to select a pixel value of a pixel at a position closest to a center of the image as a pixel in which the pixel corresponding point is most clearly reflected among pixels corresponding to the pixel corresponding points on the reference plane in the plurality of images to determine the pixel value of the pixel corresponding point.

13. An X-ray imaging apparatus comprising:
an imaging unit including an X-ray source for irradiating a subject with X-rays and an X-ray detection unit for detecting the X-rays transmitted through the subject, the imaging unit being configured to capture an original image which includes a plurality of pixels;
a moving mechanism including a top board for placing the subject thereon, the moving mechanism being capable of moving at least one of the top board and the imaging unit to change a relative position between the top board and the imaging unit; and
an image processing unit configured to
acquire a plurality of original images while changing the relative position by the moving mechanism and generate a subject image based on the plurality of original images,
set a reference plane that includes a plurality of pixel corresponding points and is an imaging region of the subject image based on the plurality of original images and determine pixel values of the plurality of pixel corresponding points included in the reference plane based on the plurality of original images coordinate-transformed on the reference plane to generate the subject image on the reference plane,
identify the original image captured with an incident of the X-ray irradiated from the X-ray source to the pixel corresponding point for each of the plurality of pixel corresponding points, and
determine the pixel value of a reached pixel of the X-ray irradiated from the X-ray source and passed through the pixel corresponding point among the plurality of pixels in the identified original image as the pixel value of the pixel corresponding point by selecting among the plurality of original images.

* * * * *